(12) United States Patent
Rooke

(10) Patent No.: US 6,692,956 B2
(45) Date of Patent: Feb. 17, 2004

(54) RECOMBINANT ADENOVIRAL VECTORS

(75) Inventor: Ronald Rooke, Illkirch (FR)

(73) Assignee: Transgene S.A., Strasbourg (FR)

( * ) Notice: Subject to any disclaimer, the term of this patent is extended or adjusted under 35 U.S.C. 154(b) by 0 days.

(21) Appl. No.: 09/969,770

(22) Filed: Oct. 4, 2001

(65) Prior Publication Data

US 2002/0106746 A1 Aug. 8, 2002

Related U.S. Application Data

(60) Provisional application No. 60/246,088, filed on Nov. 7, 2000.

(30) Foreign Application Priority Data

Oct. 6, 2000 (EP) .............................. 00440267

(51) Int. Cl.$^7$ ........................ C12N 15/63; C12N 15/00
(52) U.S. Cl. .............................. 435/320.1; 424/233.1
(58) Field of Search ............... 424/233.1; 435/320.1

(56) References Cited

U.S. PATENT DOCUMENTS

| 5,851,806 A | 12/1998 | Kovesdi et al. |
| 6,100,086 A | 8/2000 | Kaplan et al. |

FOREIGN PATENT DOCUMENTS

| EP | 0707071 A1 | 4/1996 |
| EP | 707071 A1 | 4/1996 |
| EP | 0974668 A1 | 1/2000 |
| WO | WO 96/12030 A1 | 4/1996 |
| WO | WO 99/02658 A1 | 1/1999 |

OTHER PUBLICATIONS

Harrod K. S. et al., "Adenoviral E3–14.7K Protein in LPS–induced Lung Inflammation", American Journal of Physiology, Apr. 2000, vol. 278, No. 4, Part 1, pp. L631–L639.

Krajcsi P. et al., "The Advenovirus E3–14.7K Protein and the E3–10.4K/14.5K Complex of Proteins, Which Independently Inhibit Tumor Necrosis Factor (TNF)–induced Apoptosis, Also Independently Inhibit TNF–induced Release of Arachidonic Acid.", Journal of Virology, 1996, vol. 70, No. 8, pp. 4904–4913.

Gantzer M. et al., "Constitutive Expression of the Adenovirus E3–14.7K Protein Dose Not Prolong Adenovirus Vector DNA Persistence but Protects Mice Against Lipopolysaccharide–Induced Acute Hepatitis.", Human Gene Therapy, May 2002, vol. 13, No. 8, pp. 921–933.

International Search Report, Jun. 7, 2002, for EPO Application No. 01120916.

Tollefson et al., 1996 *J. Virol.*, vol. 70, pp. 2296–2306.

Signas et al., 1982, *Nature*, vol. 299, pp. 175–178.

Burgert et al., 1985, *Cell*, vol. 41, p. 987–997.

Andersson et al., 1987, *J. Immunol.*, vol. 138, pp. 3906–3966.

Browning and Ribolini, 1989, *J. Immunol.*, vol. 143, pp. 1859–1967.

Mestan et al., 1986, *Nature*, vol. 323, pp. 816–819.

Yang et al., 1994, *Proc. Natl. Acad. Sci. USA*, vol. 91, pp. 4407–4411.

Zsengeller et al., 1995, *Human Gene Therapy*, vol. 6, pp. 457–467.

Yang et al, 1995, *J. Virology*, vol. 69, pp. 2004–2015.

Ilan et al., 1997, *Proc. Natl. Acad. Sci. USA*, vol. 94, pp. 2587–2592.

Wold et al., 1995, *Current Topics in Microbiology and Immunology*, vol. 199, pp. 237–274.

*Primary Examiner*—James Housel
*Assistant Examiner*—Stacy B. Chen
(74) *Attorney, Agent, or Firm*—Burns, Doane, Swecker & Mathis, L.L.P.

(57) ABSTRACT

The present invention concerns a recombinant adenoviral vector derived from an adenovirus genome in which at least a part of the E3 region is deleted or is non functional, wherein said adenoviral vector retains E3 sequences encoding a functional 14.7K protein, a functional 14.5K protein, and/or a functional 10.4K protein. The present invention further relates to the use of a polynucleotide comprising at least one or more gene(s) of an E3 region of an adenovirus, taken individually or in combination, to protect from an inflammatory reaction in a host cell, tissue or organism. The present invention additionally concerns a viral particle, a host cell and a composition comprising said recombinant adenoviral vector or said polynucleotide, as well as their use for therapeutic or prophylactic purpose.

13 Claims, 4 Drawing Sheets

SEQUENCE LISTING

```
<160> NUMBER OF SEQ ID NOS: 4

<210> SEQ ID NO 1
<211> LENGTH: 38
<212> TYPE: DNA
<213> ORGANISM: Artificial Sequence
<220> FEATURE:
<223> OTHER INFORMATION: 5' PCR primer for cloning Ad5 14.7K gene
      containing an AatII site at its extremity

<400> SEQUENCE: 1
tacgacgtca tgactgacac cctagatcta gaaatgga                              38

<210> SEQ ID NO 2
<211> LENGTH: 42
<212> TYPE: DNA
<213> ORGANISM: Artificial Sequence
<220> FEATURE:
<223> OTHER INFORMATION: 3' PCR primer for cloning the Ad5 14.7K gene
      containing an AatII site at its extremity

<400> SEQUENCE: 2
catgacgtct acgtattagt taaagggaat aagatctttg ag                         42

<210> SEQ ID NO 3
<211> LENGTH: 24
<212> TYPE: DNA
<213> ORGANISM: Human adenovirus type 5

<400> SEQUENCE: 3
aggtgagtga atgcagcctt cggt                                             24

<210> SEQ ID NO 4
<211> LENGTH: 26
<212> TYPE: DNA
<213> ORGANISM: Human adenovirus type 5

<400> SEQUENCE: 4
agtgatgagg ctgcagatga gcgtga                                           26
```

RECOMBINANT ADENOVIRAL VECTORS

CROSS-REFERENCE TO RELATED APPLICATIONS

This application claims priority under 35 U.S.C. §§119 and/or 365 to EP 00 44 0267.3 filed in Europe on Oct. 6, 2000; and U.S. Provisional Application No. 60/246,088 filed in the United States on Nov. 7, 2000, the entire content of which is hereby incorporated by reference.

FIELD OF THE INVENTION

The present invention concerns a recombinant adenoviral vector derived from an adenovirus genome in which at least a part of the E3 region is deleted or is non functional, wherein said adenoviral vector retains E3 sequences encoding a functional 14.7K protein, a functional 14.5K protein, and/or a functional 10.4K protein. The present invention further relates to the use of a polynucleotide comprising at least one or more gene(s) of an E3 region of an adenovirus, taken individually or in combination, to protect from an inflammatory reaction in a host cell, tissue or organism. The present invention additionally concerns a viral particle, a host cell and a composition comprising said recombinant adenoviral vector or said polynucleotide, as well as their use for therapeutic or prophylactic purpose. The invention is of very special interest in gene therapy applications and in the protection from TNF (Tumor necrosis factor) or Fas-mediated inflammatory conditions.

BACKGROUND OF THE INVENTION

Gene therapy can be defined as the transfer of genetic material into a cell or an organism. The possibility of treating human disorders by gene therapy has changed in the last few years from the stage of theoretical considerations to that of clinical applications. The first protocol applied to man was initiated in the USA in September 1990 on a patient suffering from adenine deaminase (ADA) deficiency. This first encouraging experiment has been followed by numerous new applications and promising clinical trials based on gene therapy are currently ongoing. The large majority of the current protocols employ vectors to carry the therapeutic gene to the cells to be treated.

There are two main types of gene-delivery vectors, viral and non-viral. Viral vectors are derived from naturally-occuring viruses and use the diverse and highly sophisticated mechanisms that wild-type viruses have developed to cross the cellular membrane, escape from lysosomal degradation and deliver their genome to the nucleus. Many different viruses are being adapted as vectors, but the most advanced are retrovirus, adenovirus and adeno-associated virus (AAV) (Robbins et al., 1998, Trends Biotechnol. 16, 35–40; Miller, 1997, Human Gene Therapy 8, 803–815; Montain et al., 2000, Tibtech 18, 119–128). Substantial effort has also gone into developing poxviruses (especially vaccinia) and herpes simplex virus (HPV). Non-viral approaches include naked DNA (i.e., plasmidic DNA; Wolff et al., 1990, Science 247, 1465–1468), DNA complexed with cationic lipids (for a review, see for example Rolland, 1998, Critical reviews in Therapeutic Drug Carrier Systems 15, 143–198) and particles comprising DNA condensed with cationic polymers (Wagner et al., 1990, Proc. Natl. Acad. Sci. USA 87, 3410–3414 and Gottschalk et al., 1996, Gene Ther. 3, 448–457). At the present stage of development, the viral vectors generally give the most efficient transfection but their main disadvantages include their limited cloning capacity, their tendency to elicit immune and inflammatory responses and their manufacturing difficulties. Non-viral vectors achieve less efficient transfection but have no insert-size limitation, are less immunogenic and easier to manufacture.

Adenoviruses have been detected in many animal species, are non-integrative and of low pathogenicity. They are able to infect a variety of cell types, dividing as well as quiescent cells. They have a natural tropism for airway epithelia. In addition, they have been used as live enteric vaccines for many years with an excellent safety profile. Finally, they can be easily grown and purified in large quantities. These features have made adenoviruses particularly appropriate for use as gene therapy vectors for therapeutic and vaccine purposes. Their genome consists of a linear double-standed DNA molecule of approximately 36 kb carrying more than about thirty genes necessary to complete the viral cycle. The early genes are divided into 4 regions dispersed in the adenoviral genome (E1 to E4). The E1, E2 and E4 regions are essential for viral replication. Early region 3 (E3) has been termed a "non essential region" based on the observation that naturally occuring mutants or hybrid viruses deleted within the E3 region still replicate like wild-type viruses in cultured cells (Kelly and Lewis, 1973, J. Virol. 12, 643–652). The late genes (L1 to L5) encode in their majority the structural proteins constituting the viral capsid. They overlap at least in part with the early transcription units and are transcribed from a unique promoter (MLP for Major Late Promoter). In addition, the adenoviral genome carries at both extremities cis-acting regions essential for DNA replication, respectively the 5' and 3' ITRs (Inverted Terminal Repeats) and a packaging sequence.

The E3 region spans map units (MU) 76.6–86.2 (nucleotides 27329 to 31103 in Ad5) and is controlled by its own promoter (E3 promoter) that is quite stringently dependent on the presence of E1 transcription factors for expression. Transcription occurs from left to right with regards to the adenoviral genome (sense orientation) and produces a variety of different mRNA species which differ both in their splicing patterns and in poly A site utilization. Among the nine proteins which are potentially encoded by the mRNAs which initiate from the E3 promoter, seven have been clearly identified. They have been named according to their estimated molecular weight, respectively 19, 14.7, 14.5, 12.5, 11.6, 10.4 and 6.7 kDa. To date, the function of only five of them can be assigned. The E3 11.6K protein is involved in the lysis of adenovirus-infected cells (Tollefson et al., 1996, J. Virol. 70, 2296–2306) whereas the E3-gp19K, 10.4K, 14.5K and 14.7K proteins are immunomodulatory proteins allowing an attenuation of the host immune response against adenovirus-infected cells.

The best characterized of the E3 protein, E3-gp19K, is an integral membrane protein anchored in the membrane of the endoplasmic reticulum (ER). In vitro studies have established that the E3 gp19K protein blocks cytolysis by CTLs (Cytotoxic T lymphocytes) by binding major histocompatibility complex (MHC) class I antigens (Signas et al., 1982, Nature 299, 175–178). This interaction results in the retention of class I molecules in the ER, thus preventing their cell-surface expression (Burgert et al., 1985, Cell 41, 987–997) and, ultimately, recognition of adenovirus-infected cells by CTLs (Andersson et al., 1987, J. Immunol. 138, 3960–3966).

Tumor Necrosis Factor α (TNFα) has been shown to be important for adenovirus clearance during infection. TNFα is a potent cytokine responsible for a wide variety of physiologic and immunologic effects. It is secreted by activated macrophages and lymphocytes in response to virus infections, tissue damages, bacterial endotoxins and other cytokines. TNFα binds to specific receptors, leading to activation of signal transduction pathways, transcription factors and protein kinases. In addition, TNFα is cytotoxic to a wide variety of primary tumors and transformed cell lines (Browning and Ribolini, 1989, J. Immunol. 143, 1859–1967). TNFα can also suppress the replication of both DNA and RNA viruses in infected cells (Mestan et al., 1986, Nature 323, 816–819). TNF activates phospholipase A2 (PLA2), resulting in the release of arachidonic acid (AA) which are responsible for the establishment of an inflammmatory status.

A number of experimental evidences suggest that three E3-encoded proteins, respectively 14.7K, 10.4K and 14.5K inhibit TNFα-induced cytolysis and TNF-induced release of AA (Krajcsi et al., 1996, J. Virol. 70, 4904–4913). The 14.7K protein is a hydrophilic protein found in the soluble fractions of both cytosol and nucleus of adenovirus-infected cells. The mechanism by which the 14.7K protein inhibits TNFα-mediated cytolysis, is not fully defined but it probably interferes with the TNFα receptor signaling pathway.

E3 10.4K and E3 14.5K proteins are integral membrane proteins that act as a complex (named RID complex for receptor internalization and degradation) to protect cells from the lytic effect of TNFα (Gooding et al., 1991, J. Virol. 65, 4114–4123). These proteins have an additional function in cell surface receptor modulation and have been shown to accelerate internalization of the epidermal growth factor receptor, the insulin receptor and Fas receptor (Fas) by targeting them to lysosomes for degradation (Steward et al., 1995, J. Virol. 69, 172–181; Shisler et al., 1997, J Virol. 71, 8299–8306; Tollefson et al., 1998, Nature 392, 726–730). The nature of the interaction between the RID complex and these cellular proteins is unknown. Fas is expressed on numerous tissues and especially on T cells, hepatocytes, heart and kidney cells. It is central in the homeostasis of a number of organs as well as the immune system but also in the elimination of virus-infected cells by CTLs.

The redundant anti-TNF functions encoded by the adenoviruses leads are presumed to be relevant to viral pathogenesis. The actual contribution of the E3-encoded TNFα antagonists to the maintenance of the virus in an infected host has not yet been investigated, apart from the observation that expression of the E3-14.7K gene in the respiratory epithelium of transgenic mice reduces lung inflammation and enhances adenoviral vector gene expression.

Moreover, TNFα and Fas are also implicated in a number of pathological conditions. For example, high levels of TNFα are associated with acute hepatotoxicity in many animal models including lipopolysaccharides (LPS) and ConA-induced liver injury. It is an important mediator in septic shock and fulminant hepatic failure (Jo et al., 2000, Nat. Med. 6, 564). High levels of circulating TNF have poor prognostic values in patients with viral hepatitis B and C or with alcoholic liver disease (reviewed in Bradham et al., 1998, The American Journal of Physiology 275, 4387). Cumulative evidence suggests the contribution of Fas associated with Fas ligand (FasL) to inflammatory and tissue-damages. A role of these molecules has been shown in alcohol-induced cirrhosis, hepatitis, graft rejection and autoimmune diseases.

The adenoviral vectors presently used in gene therapy protocols lack most of the E1 region which renders the viruses replication-deficient to avoid their dissemination in the environment and the host organism. Moreover, most of the adenoviral vectors are also E3 deleted, in order to increase their cloning capacity. The feasability of gene transfer using these vectors has been demonstrated into a variety of tissues in vivo (see for example Yei et al.,1994, Hum. Gene Ther. 5, 731–744; Dai et al., 1995, Proc. Natl. Acad. Sci. USA 92, 1401–1405; Howell et al., 1998, Hum. Gene Ther. 9, 629–634; Nielsen et al., 1998, Hum. Gene Ther. 9, 681–694; U.S. Pat. Nos. 6,099,831; 6,013,638). However, their use is associated with acute inflammation and toxicity in a number of animal models (Yang et al., 1994, Proc. Natl. Acad. Sci. USA 91, 4407–4411; Zsengeller et al., 1995, Hum. Gene Ther. 6, 457–467) as well as with host immune responses to the viral vector and gene products (Yang et al., 1995, J. Virol. 69, 2004–2015), resulting in the elimination of the infected cells and transient gene expression.

The persistence of gene expression is a prerequisite before envisaging the wide use of adenoviral vectors in human gene therapy protocols, in particular in view of treatment of chronic and genetic diseases. With the goal of improving adenovirus-mediated gene expression, it has been suggested to engineer adenoviral vectors expressing the E3-encoded proteins and the presently available studies have been conducted with the entire E3 region. The European patent application EP707071 discloses recombinant adenoviruses having a foreign gene inserted in replacement of the E1 region and retaining the full-sized wild-type E3 region driven by its own promoter. Experimental data demonstrate the capability of these E1$^-$ E3$^+$ adenoviruses to express the foreign gene product and provide therapeutic effect in various animal models, but, in the absence of any comparative data, the benefit of retaining the entire E3 region over an E3-deleted virus was not clearly established. Long-term gene expression and attenuation of the antiviral immune response was observed in a rat model injected with a E1-deleted recombinant adenovirus containing the entire E3 region driven by a strong and constitutive promoter (Ilan et al., 1997, Proc. Natl. Acad. Sci. USA 94, 2587–2592). However, none of these studies have investigated whether the maintenance of the entire E3 region has a protective effect on the inflammation and toxicity generally observed with the conventional adenoviral vectors which are responsible for rapid elimination of the infected host cells, a transient gene expression and activation of pro-inflammatory substances that have pleiotropic effects.

SUMMARY OF THE INVENTION

The invention provides adenoviral vectors for gene therapy that retain the gene(s) of the E3 region encoding the 14.7K protein and/or the RID complex (formed by the association of the 10.4K and 14.5K proteins). It was surprisingly found that, when used in a murine model of TNF-induced liver pathology, the 14.7K-expressing adenoviral vector protects the animal from death by inflammatory reactions. In a similar model, the RID-expressing adenoviral vector inhibits acute hepatitis induced by an anti-Fas antibody. These results validate the functionality of these vectors for protecting infected cells, tissues or organisms from inflammation.

Thus, the technical problem underlying the present invention is the provision of recombinant adenoviral vectors which do not have a number of drawbacks associated with conventional vectors disclosed for this purpose so far and of means which allow protection from an inflammation condition, especially mediated by TNF or Fas or induced by administration of gene therapy (adenoviral) vectors.

This problem is solved by the provision of the embodiments characterized in the claims.

Accordingly, the present invention relates to a recombinant adenoviral vector derived from an adenovirus genome in which at least a part of the E3 region is deleted or is non functional, wherein said adenoviral vector retains E3 sequences encoding:

(i) a functional 14.7K protein, (ii) a functional 14.5K protein, (iii) a functional 10.4K protein, and/or wherein said recombinant adenoviral vector comprises a gene of interest, and wherein said retained E3 sequences and said gene of interest are operably linked to regulatory elements allowing their expression in a host cell.

DETAILED DESCRIPTION OF THE PREFERRED EMBODIMENTS

Figure 1:
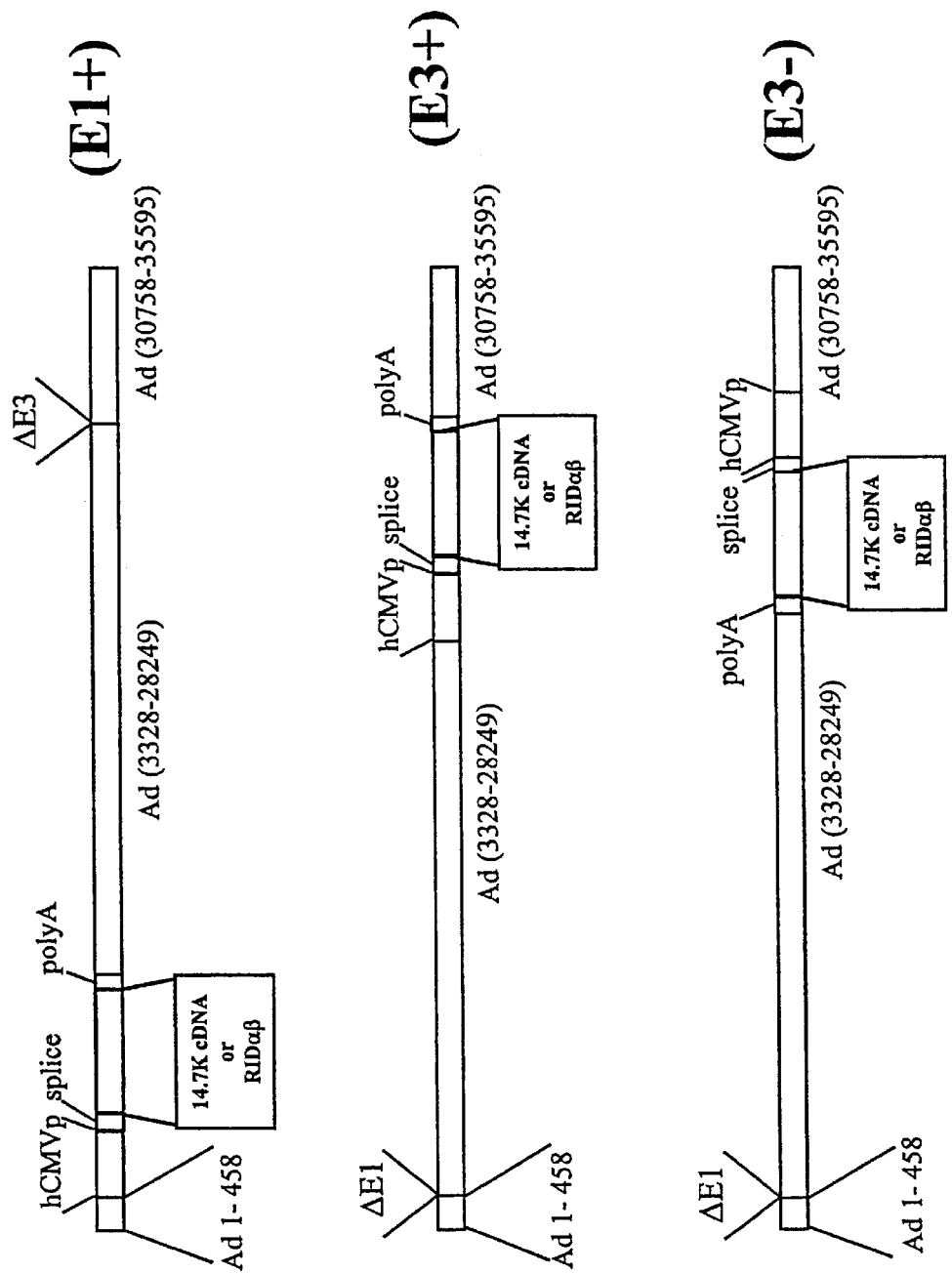
FIG. 1 represents schematically the adenoviral vector expressing the 14.7K and RID-expressing genes. The genes are placed under the control of the early CMV promoter (hCMVp), a chimeric intron (splice) and SV40 polyadenylation sequence (poly A) and inserted either in replacement of the deleted E1 region (deletion of nt 459 to 3327) in sense orientation (E1+) or in replacement of the deleted E3 region (deletion of nt 28250 to 30757) in sense (E3+) or anti-sense (E3−) orientation.

The term "derived" as used herein means that apart from the above described features, the adenovirus genome which is taken as source to construct the adenoviral vector of the invention remains unchanged and contains a 5' ITR, a packaging sequence, a E1 region, a E2 region, a partially deleted E3 region retaining one or more of the precited E3 genes, a E4 region, the late genes and a ITR 3'. However, within the scope of the present invention, the source adenovirus genome may also be modified according to methods known by the person skilled in the art (as indicated hereinafter), as long as the features described above are contained.

The retained E3 sequences used in the context of the present invention are capable alone or in combination, directly or by means of other cellular or viral factors to protect at least partially from an inflammation condition, and especially from TNF and/or Fas-induced inflammation. They may also provide protection against toxicity (e.g., hepatotoxicity) and allow a prolonged expression of the gene of interest carried by the adenoviral vector of the present invention.

Although the E3 region may vary between the different adenovirus strains, it can be identified on the basis of nucleotide and amino acid sequences available in different sources (Wold et al., 1995, Current Topics in Microbiology and Immunology 199, 237–274, which is incorporated herein in its entirety) or by homology with the well characterized Ad5 E3 region (sequence disclosed in Genbank under accession number M73260 for Ad5 and K02559 for Ad2, in Chroboczek et al., 1992, Virol. 186, 280–285 and U.S. Pat. No. 6,040,174 which are incorporated herein in their entirety). As an indication, the E3 region is located at the right end of the adenoviral genome (between 76.6–86.2 map units of the Ad5 genome), with the E3 promoter being present at the extreme left portion of the E3 region. In particular, in the Ad5 genome, the 14.7K-encoding gene extends from nucleotides (nt) 30453 to 30839, the 14.5K-encoding gene extends from nt 30062 to 30459 and the 10.4K-encoding gene extends from nt 29884 to 30059. In the context of wild-type adenovirus infection, the 14.5K and 10.4K proteins making up the RID complex are thought to be translated from the same RNA.

The person skilled in the art is able to modify the native E3 region of an adenoviral genome by conventional molecular biology techniques in order to obtain an E3 region which retains one or more of the above-mentioned E3 genes and have the non-retained E3 sequences being altered (non functional) or deleted. In particular, it is well within the reach of the person skilled in the art to delete from an adenoviral E3 region a specific portion of DNA, e.g., by appropriate restriction or endonuclease digest and religation. Another possibility is to isolate the retained E3 sequences by PCR.

Preferably, the recombinant adenoviral vector of the present invention retains the entire coding sequences of one or more of the above-mentioned E3 sequences extending from the initiator ATG to the stop codon. However, it is also feasible to employ a variant provided that the protective capacities against inflammation of its expression product be preserved. Variant refers to a acid nucleic differing from the concerned native E3 sequence but whose encoded product retains essential properties thereof. Generally, variants are obtained by deletion, addition and/or substitution of one or more nucleotides or of a sequence of nucleotides at any position of the native sequence. Such modifications can be obtained by standard recombinant techniques (i.e., mutation, enzyme restriction cutting and religation, PCR techniques and the like). Advantageously, in the context of the present invention, a variant shares a high degree of homology with the native E3 sequence, in particular at least 70% sequence identity, more preferably at least 80% and even more preferred at least 90%. Particularly preferred is absolute identity. By a variant having 70% sequence identity with the native sequence, it is intended that the nucleotide sequence may include up to 30 point mutations per each 100 nucleotides of the native nucleotide sequence, which can be either silent or result in a modification of an encoded amino acid residue. As a practical matter, whether a particular variant is at least 70% identical to a reference sequence (the native E3 sequence), can be determined conventionnally using known computer programs. A preferred method for determining the best overall match between the variant and the native sequences, also referred as a global sequence alignment, can be determined using the FASTDB computer program based on the algorihm of Brutlag et al. (1990, Comp. App. Biosci. 6, 237–245).

It is possible for the person skilled in the art to determine whether a variant is functional (capable of protecting a cell, tissue or organism from an inflammation condition as defined hereinafter). The functionality of a variant can be easily determined by comparing the anti-inflammatory property displayed by the expression product of the variant with the anti-inflammatory property displayed by the expression product of its related native E3 sequence, either in vitro (by evaluating the associated function of the expression product in appropriate cultured cells, e.g., down-regulation of EGF receptor, inhibition of Fas- or TNF-mediated apoptosis), or in vivo (in inflammation animal models such as galactosamine and LPS or anti-Fas antibody-injected mice that, respectively, reproduce TNF or Fas-mediated inflammation). In vitro and in vivo experimental conditions for analysing anti-inflammatory properties are provided in Examples 1 and 2 of the present specification. However, other methods well known by those skilled in the art, are also usable in the context of the invention. Preferably, a variant used in the present invention exhibit anti-inflammatory properties to approximately the same extend as or to a greater extend than the native E3 sequence.

According to a first alternative, the recombinant adenoviral vector according to the present invention retains the E3 sequences encoding a functional 14.7K protein. In a particular embodiment, the retained E3 sequences consist in the E3 gene encoding the native 14.7K protein.

According to a second alternative, the recombinant adenoviral vector according to the present invention retains the E3 sequences encoding both functional 14.5K and 10.4K proteins. According to a preferred embodiment, both sequences are arranged as a dicistron (controlled by the same promoter), the 10.4K-encoding sequence preceding the 14.5K-encoding sequence and the stop codon of the 10.4K-encoding sequence being separated by 2 bp from the start codon of the 14.5K-encoding sequence (as found in the wild type context). It has been observed that this configuration is advantageous to obtain efficient production of both 10.4K and 14.5K proteins. In a particular embodiment, the retained E3 sequences consist of the E3 genes encoding both the native 14.5K and 10.4K proteins. It is also possible to express E3 10.4K-encoding sequence and 14.5K-encoding sequence as independent cistrons (controled by independent promoters) inserted either in the same adenoviral vector (same or different location) or in two separate adenoviral vectors.

According to the embodiment following which the adenoviral vector of the present invention encodes functional 14.5K and 10.4K proteins, it is preferred that said proteins are able to associate in a host cell to form a complex, e.g., the so-called RID complex.

The E3 sequences retained in the adenoviral vector of the invention are operably linked to regulatory elements allowing their expression in a host cell. "Operably linked" refers to a juxtaposition of regulatory elements and a gene of interest, which are in relationship permitting them to operate in the expected manner. For instance, a promoter is operably linked to a gene of interest if the promoter allows transcription of the gene. Ther may be additional residues between the promoter and the gene of interest so long as their functional relationship is preserved.

Such regulatory elements can be the natural regulatory elements (e.g., the E3 promoter). According to another and preferred alternative, the retained E3 sequences are placed under the control of a heterologous promoter which can be constitutive or regulatable (inducible or tissue-specific). Representative examples of suitable promoters include without limitation (i) viral promoters such as the SV40 (simian virus 40) promoter, the promoter of the Herpes Simplex Virus thimidine kinase gene (TK-HSV-1), the LTR of the Rous sarcoma virus (RSV), and the adenoviral major late promoter (MLP) and (ii) any cellular promoter that control the transcription of protein-encoding genes in higher eukaryotes, such the promoters of the constitutive PGK (phosphoglycerate kinase) gene (Adra et al., 1987, Gene 60, 65–74), of the liver-specific alpha1-antitrypsin and FIX genes, of the smooth muscle cell-specific SM22 gene (Moessler et al., 1996, Development 122, 2415–2425; EP00440208.7). The immediate early promoter of the cytomegalovirus (CMV promoter) is preferred in the context of the present invention (Boshart et al., 1985, Cell 41, 521).

In order to stabilize expression, it may be advantageous that the retained E3 sequences comprise splicing sequences. They may be homologous (to the E3 sequences) or heterologous (i.e., derived from any eukaryotic gene or of synthetic origin). Splicing sequences have been published in the literature and can be readily obtained by those skilled in the art. Illustrative examples include the splicing sequences isolated from the genes encoding α or β globin (rabbit or human), apolipoprotein, immunoglobulin, factor IX, factor VIII and CFTR and the chimeric splicing sequences present in the pCI vector (Promega) made of the human β globin donor fused to the mouse immunoglobin acceptor.

The E3 sequences retained in the adenoviral vector according to the invention may be those naturally occurring in such a vector. In particular, they may remain at their natural location. However, it is also possible that the vector is constructed by deleting all E3 sequences, in particular the entire E3 region, and inserting the retained E3 sequences from the same or other adenovirus backbones in the adenoviral vector at a location where the E3 region normally resides or at a different location, e.g., in place of the deleted E1 region.

Preferably, the E3 sequences overlapping with essential viral genes are not deleted (e.g., the 12.5K-encoding E3 sequences present at the 5' extremity of the E3 region which overlap with the L4 late gene). Should the E3 sequences overlapping with an essential viral gene be deleted or altered (e.g., by mutation) in such a way that the production of the essential gene product is inhibited, it is possible to complement in trans the production of the essential viral product, either via a complementing cell line or a helper virus.

In a preferred embodiment, the adenoviral vector of the invention does not retain the sequences encoding the E3 gp19K protein.

The retained E3 sequences can be oriented in sense or anti-sense with respect to the direction of transcription of the wild-type region in which they are located. In particular, when the adenoviral vector of the present invention retains the E3 sequences encoding a functional 14.7K protein, it is preferred to insert said retained E3 sequences either (i) at a location where the E3 region normally resides and in anti-sense orientation relative to the direction of transcription of the native E3 region or (ii) where the E1 region normally resides and in sense orientation relative to the direction of transcription of the native E1 region. Referring to the embodiment of the adenoviral vector that retains the E3 sequences encoding a functional 14.5K protein and a functional 10.4K protein, it is preferred to insert said retained E3 sequences at a location where the E3 region normally resides and in sense orientation relative to the direction of transcription of the native E3 region.

The adenoviral vector according to the invention may be engineered to be conditionally replicative (CRAd vectors) in order to replicate selectively in specific host cells (i.e., proliferative cells) as described in Heise and Kirn (2000, J. Clin. Invest. 105, 847–851).

According to another and preferred alternative, the adenoviral vector of the invention is replication-defective, at least by total or partial deletion of the E1 region and/or mutation of one or more genes constituting the E1 region. Advantageously, the E1 deletion covers approximately the nucleotides 459 to 3328 or 459 to 3510, by reference to the sequence of the human adenovirus type 5 (disclosed in the Genbank under the accession number M 73260 and in Chroboczek et al., 1992, Virol. 186, 280–285). Preferably the E1 sequences overlapping with the pIX gene are not deleted.

Furthermore, the adenoviral backbone of the vector may comprise additional modifications [deletion, insertion and/or mutation of one or more nucleotide(s) in one or more viral gene(s)]. The adenoviral sequence may also be deleted of all or part of the E2 region An example of an E2 modification is illustrated by the thermosensible mutation of the DBP (DNA Binding Protein) encoding gene (Ensinger et al., 1972, J. Virol. 10, 328–339). The adenoviral sequence may also be deleted of all or part of the E4 region. A partial deletion retaining the ORFs 3 and 4 or ORFs 3 and 6/7 may be advantageous (see for example European application EP 974 668 and WO00/12741). Adenoviral vectors retaining the ITRs and packaging sequences and containing substantial genetic modifications aimed to abolish the residual synthesis of the viral antigens may also be envisaged (WO94/28152; Lusky et al., 1998, J. Virol 72, 2022–2032).

Adenoviruses adaptable for use in accordance with the present invention, can be derived from any human or animal source, in particular canine (e.g., CAV-1 or CAV-2; Genbank ref CAV1GENOM and CAV77082 respectively), avian (Genbank ref AAVEDSDNA), bovine (such as BAV3; Seshidhar Reddy et al., 1998, J. Virol. 72, 1394–1402), murine (Genbank ref ADRMUSMAV1), ovine, feline, porcine or simian adenovirus or alternatively from a hybrid thereof. Any serotype can be employed. However, the human adenoviruses of the C sub-group are preferred and especially adenoviruses 2 (Ad2) and 5 (Ad5). Generally speaking, the cited viruses are available in collections such as ATCC and have been the subject of numerous publications describing their sequence, organization and biology, allowing the artisan to apply them. For example, the sequence of the human adenovirus type 5 is disclosed in the Genebank data base (accession M 73260) and in Chroboczek et al. (1992, Virol. 186, 280–285) and is incorporated by reference in its entirety.

As mentioned before, the adenoviral vector of the invention is recombinant and comprises a gene of interest operably linked to regulatory elements allowing its expression in a host cell.

The term "gene of interest" refers to a nucleic acid which can be of any origin and isolated from a genomic DNA, a cDNA, or any DNA encoding a RNA, such as a genomic RNA, a mRNA, an anti-sense RNA, a ribosomal RNA, a ribozyme or a transfer RNA. The gene of interest can also be an oligonucleotide (i.e., a nucleic acid having a short size of less than 100 bp). It can be engineered from genomic DNA to remove all or part of one or more intronic sequences (i.e., minigene)

In a preferred embodiment, the gene of interest in use in the present invention, encodes a gene product of therapeutic interest. A "gene product of therapeutic interest" is one which has a therapeutic or protective activity when administered appropriately to a patient, especially a patient suffering from a disease or illness condition or who should be protected against this disease or condition. Such a therapeutic or protective activity can be correlated to a beneficial effect on the course of a symptom of said disease or said condition. It is within the reach of the man skilled in the art to select a gene encoding an appropriate gene product of therapeutic interest, depending on the disease or condition to be treated. In a general manner, his choice may be based on the results previously obtained, so that he can reasonably expect, without undue experimentation, i.e., other than practicing the invention as claimed, to obtain such therapeutic properties.

In the context of the invention, the gene of interest can be homologous or heterologous to the host cell into which it is introduced. Advantageously, it encodes a polypeptide, a ribozyme or an anti-sense RNA. The term "polypeptide" is to be understood as any translational product of a polynucleotide whatever its size is, and includes polypeptides having as few as 7 residues (peptides), but more typically proteins. In addition, it may be from any origin (prokaryotes, lower or higher eukaryotes, plant, virus etc). It may be a native polypeptide, a variant, a chimeric polypeptide having no counterpart in nature or fragments thereof. Advantageously, the gene of interest in use in the present invention encodes at least one polypeptide that can compensate for one or more defective or deficient cellular proteins in an animal or a human organism, or that acts through toxic effects to limit or remove harmful cells from the body. A suitable polypeptide may also be immunity conferring and acts as an antigen to provoke a humoral or a cellular response, or both.

Representative examples of polypeptides encoded by the gene of interest include without limitation polypeptides selected from the group consisting of:

polypeptides involved in the cellular cycle, such as p21, p16, the expression product of the retinoblastoma (Rb) gene, kinase inhibitors (preferably of the cyclin-dependent type), GAX, GAS-1, GAS-3, GAS-6, Gadd45 and cyclin A, B and D;

apoptosis inducers, such as p53, Bas, Bcl2, BclX, Bad and their antagonists;

angiogenic polypeptides, such as members of the family of vascular endothelial growth factors (VEGF; i.e., heparin-binding VEGF Genbank accession number M32977), transforming growth factor (TGF, and especially TGFα and β), epithelial growth factors (EGF), fibroblast growth factor (FGF and especially FGFα and β), tumor necrosis factors (TNF, especially TNFα and β), CCN (including CTGF, Cyr61, Nov, Elm-1, Cop-1 and Wisp-3), scatter factor/hepatocyte growth factor (SH/HGF), angiogenin, angiopoietin (especially 1 and 2), angiotensin-2, plasminogen activator (tPA) and urokinase (uPA;

cytokines (including interleukins, in particular IL-2, IL-6, IL-8, IL-12, colony stimulating factors such as GM-CSF, G-CSF, M-CSF), IFNα, IFNβ or IFNγ;

polypeptides capable of decreasing or inhibiting a cellular proliferation, including antibodies, toxins, immunotoxins, polypeptides inhibiting an oncogen expression products (e.g., ras, map kinase, tyrosine kinase receptors, growth factors), Fas ligand, suicide gene products, polypeptides activating the host immune system (MUC-1, early or late antigen(s) of a papilloma virus and the like);

polypeptides capable of inhibiting a bacterial, parasitic or viral infection or its development, such as antigenic determinants, transdominant variants inhibiting the action of a viral native protein by competition (EP 614980, WO95/16780), the extracellular domain of the HIV receptor CD4 (Traunecker et al., 1988, Nature 331, 84–86), immunoadhesin (Capon et al., 1989, Nature 337, 525–531; Byrn et al., 1990, Nature 344, 667–670), immunotoxins (Kurachi et al., 1985, Biochemistry 24, 5494–5499) and antibodies (Buchacher et al., 1992, Vaccines 92, 191–195);

immunostimulatory polypeptides such as B7.1, B7.2, ICAM and the like;

enzymes, such as urease, renin, thrombin, metalloproteinase, nitric oxide synthases (eNOS and iNOS), SOD, catalase, heme oxygenase, the lipoprotein lipase family;

oxygen radical scavengers; enzyme inhibitors, such as alpha1-antitrypsin, antithrombin III, plasminogen activator inhibitor PAI-1, tissue inhibitor of metalloproteinase 1–4;

polypeptides capable of restoring at least partially a deficient cellular function responsible of an pathological condition, such as dystrophin or minidystrophin (in the context of myopathies), insulin (in the context of diabetes) coagulation factors (FVIII, FIX in the context of hemophilia), CFTR (in the context of cystic fibrosis);

angiogenesis inhibitors, such as angiostatin, endostatin, platelet factor-4;

transcription factors, such as nuclear receptors comprising a DNA binding domain, a ligand binding domain and domain activating or inhibiting transcription (e.g., fusion products derived from oestrogen, steroid and progesterone receptors);

markers (-galactosidase, CAT, luciferase, GFP . . . ); and any polypeptides that are recognized in the art as being useful for the treatment or prevention of a clinical condition.

It is within the scope of the present invention that the gene of interest may include addition(s), deletion(s) and/or modification(s) of one or more nucleotide(s) with respect to the native sequence.

In the context of the invention, the term "suicide gene" encompasses any gene whose product is capable of converting an inactive substance (prodrug) into a cytotoxic substance, thereby giving rise to cell death. The gene encoding the thymidine kinase (TK) of HSV-1 constitutes the prototype of the suicide gene family (Caruso et al., 1993, Proc. Natl. Acad. Sci. USA 90, 7024–7028; Culver et al., 1992, Science 256, 1550–1552), and catalyzes the transformation of nucleoside analogs (prodrug) such as acyclovir or ganciclovir to toxic nucleosides that are incorporated into the neoformed DNA chains, leading to inhibition of cell division. A large number of suicide gene/prodrug combinations are currently available. Those which may more specifically be mentioned are the bacterial and fungal genes encoding cytosine deaminase (Erbs et al., 1997, Curr. Genet. 31, 1–6; WO93/01281; EP 402 108) and uracil phosphoribosyl transferase (Anderson et al., 1992, Eur. J. Biochem. 204, 51–56; Kern et al., 1990, Gene 88, 149–157), which can be used with the prodrug 5-fluorocytosine (5-FC). The present invention also encompasses the use of mutant suicide genes, such as those described in WO96/16183 and WO99/54481.

As mentioned above, the gene of interest also includes genes encoding anti-sense sequences and ribozymes capable of binding and inactivating specific cellular RNA, preferably that of selected positively-acting growth regulatory genes, such as oncogenes and protooncogenes (c-myc, c-fos, c-jun, c-myb, c-ras, Kc and JE).

As mentioned above, the gene of interest is operably linked to regulatory elements allowing its expression in a host cell. Such regulatory elements include a promoter that may be obtained from any viral, bacterial or eukaryotic gene (even from the gene of interest) and be constitutive or regulable. Optionally, it can be modified in order to improve its transcriptional activity, delete negative sequences, modify its regulation, introduce appropriate restriction sites etc. Suitable promoters include but are not limited to the followings: adenoviral E1a, MLP, PGK, MT (metallothioneine; Mc Ivor et al., 1987, Mol. Cell Biol. 7, 838–848), α-1 antitrypsin, CFTR, surfactant, immunoglobulin, β-actin, SRα, SV40, RSV LTR, TK-HSV-1, SM22, Desmin (WO 96/26284) and early CMV. Alternatively, one may employ a promoter capable of being activated in proliferative cells isolated from genes overexpressed in tumoral cells, such as the promoters of the MUC-1 gene overexpressed in breast and prostate cancers (Chen et al., 1995, J. Clin. Invest. 96, 2775–2782), of the CEA (Carcinoma Embryonic Antigen)-encoding gene overexpressed in colon cancers (Schrewe et al., 1990, Mol. Cell. Biol. 10, 2738–2748), of the ERB-2 encoding gene overexpressed in breast and pancreas cancers (Harris et al., 1994, Gene Therapy 1, 170–175) and of the α-foetoprotein-encoding gene overexpressed in liver cancers (Kanai et al., 1997, Cancer Res. 57, 461–465).

The regulatory elements controlling the expression of the gene of interest may further comprise additional elements, such as exon/intron sequences, targeting sequences, transport sequences, secretion signal sequences, nuclear localization signal sequences, IRES, polyA transcription termination sequences, tripartite leader sequences, sequences involved in replication or integration. These elements have been reported in the literature and can be readily obtained by those skilled in the art.

The adenoviral vector of the present invention may comprise one or more gene(s) of interest. In this regard, the combination of genes encoding a suicide gene product and a cytokine (such as IL-2, IL-8, IFNγ, GM-CSF) or an immunostimulatory polypeptide (such as B7.1, B7.2, ICAM and the like) may be advantageous in the context of the invention. The different genes of interest may be controled by the same (polycistronic) or separate regulatory elements which can be inserted into various sites within the vector in the same or opposite directions.

The present invention also provides the use of a polynucleotide comprising at least one or more gene(s) of an E3 region of an adenovirus, taken individually or in combination, to protect a host cell, tissue or organism from an inflammatory condition. Preferably, said gene(s) of an E3 region of an adenovirus is (are) selected from the group consisting of genes encoding functional 14.7K, 14.5K and 10.4K proteins.

The finding that the expression of certain genes of the adenoviral E3 region is advantageous for inflammation protection is also of importance for obtaining such effect in expression vectors other than adenoviral vectors. Thus, one or more genes of an adenoviral E3 region can generally be used to achieve protection of an inflammatory condition mediated by various factors, either cellular factors (e.g., TNF and/or Fas) or extracellular factors (e.g., a recombinant adenoviral vector expressing a gene of interest, especially a cytotoxic gene).

The term "polynucleotide" as used herein defines a polymeric form of any length of nucleotides or analogs thereof. It includes any possible nucleic acid (RNA, DNA), in particular DNA, which can be single or double stranded, linear or circular, natural or synthetic. A polynucleotide may comprise modified nucleotides, such as methylated nucleotides and nucleotide analogs (see U.S. Pat. Nos. 5,525,711, 4,711,955 or EPA 302 175 as examples of modifications). Such a polynucleotide can be obtained from existing nucleic acid sources (e.g., genomic, cDNA) but can also be synthetic (e.g., produced by oligonucleotide synthesis). Its sequence may be interrupted by non-nucleotide elements. A polynucleotide may be further modified after polymerization.

As indicated before, the E3 region may vary between the different adenovirus strains. However, it is well within the skill of the person skilled in the art to identify the E3 region of an adenovirus as well as the genes contained in it. Thus, it is possible for the person skilled in the art to isolate a polynucleotide comprising at least one or more gene(s) of an E3 region from an adenoviral genome in order to use it (them) according to the invention. With respect to the E3 genes and the regulatory elements controling their expression, the same applies as already described in connection with the adenoviral vector according to the invention.

The E3 gene(s) is (are) capable alone or in combination, directly or by means of other cellular or viral factors to protect a host cell, tissue or organism from an inflammatory condition. The expression "to protect a host cell, tissue or organism from an inflammatory condition" as used herein refers to an improvement of an inflammatory status in the presence of the polynucleotide used according to the invention compared to its absence or absence of expression. As a result, the host cell, tissue or organism expressing said polynucleotide is less prone to inflammation or is recovering more rapidly or more efficiently than a host cell, tissue or organism not containing or not expressing said polynucleotide. Such an improvement of an inflammatory status can be determined by measuring the concentration of one or several inflammatory markers that are produced in the course of the inflammation reaction, such as TNF, IL-1β, IL-6, IL-8, IL-12 and/or IFNβ (a reduction by a factor of two or more of at least one of these markers present in the blood circulation and/or associated to their cognate receptor could indicate an improvement of an inflammatory status), or by pathological analysis of organs (an observed reduction of lymphocyte infiltration could be interpreted as an improvement of an inflammatory status) or by measuring the rate of survival of animal mimicking an inflammatory condition (an increase of the survival rate by a factor of at least 2 over a period of time of at least 3 days could be interpreted as an improvement of an inflammatory status). One way to proceed is to inject in a mouse a polynucleotide carrying the retained E3 gene(s) and a product allowing the establishment and/or the development of an inflammatory condition (e.g., glucosamine and LPS for inducing a TNF-mediated inflammation, anti-Fas antibodies for inducing a Fas-mediated inflammation, adenoviral particles for inducing an adenovirus-mediated inflammation) and to determine the survival rate over a period of several days compared to control mice that have not received the E3-expressing polynucleotide.

Optionally, the polynucleotide in use in the context of the invention may additionally reduce or inhibit a toxic reaction which are often associated with inflammatory conditions (especially hepatotoxicity). The improvement of a toxic status can be determined by measuring the serum level of one or several markers that are produced in the course of a toxic reaction, such as transaminases generally associated with hepatotoxicity (a reduction by a factor of two or more could indicate an improvement of a toxic status), or by pathological analysis of organs (observable reduction of necrosis or tissue degeneration could indicate an improvement of a toxic status) or by measuring the rate of survival of animal mimicking a toxic reaction (an increase of the survival rate by a factor of at least 2 over a period of time of at least 3 days could be interpreted as an improvement of a toxic status).

A preferred embodiment of the present invention encompasses a polynucleotide comprising (i) a gene of an E3 region of an adenovirus encoding a functional 14.7K protein or (ii) genes of an E3 region of an adenovirus encoding a functional 14.5K protein and a functional 10.4K protein. In this regard, it is preferred that said functional 14.5K protein and said functional 10.4K protein are able to associate in a host cell to form a complex, i.e., the so-called RID complex. In a particular embodiment, the polynucleotide consists in either the E3 gene encoding the 14.7K protein or the E3 genes encoding both the 14.5K and the 10.4K proteins.

Preferably, the E3 gene(s) in use in the present invention comprise(s) the complete coding sequence, i.e., from the initiator ATG codon to the stop codon. However, it is possible to employ a functional variant of such an E3 gene, i.e., a variant obtained by deletion, mutation or truncation which still encode a functional E3 product, as defined previously.

The E3 gene(s) used in the scope of the present invention may be from any adenoviral origin (animal or human) as cited above. Preferably they are derived from a human adenovirus of sub-group C, particularly preferred from Ad2 or Ad5.

The E3 gene(s) present in the polynucleotide used in the present invention is (are) operably linked to regulatory elements to allow its (their) expression in a host cell, tissue or organism. Such elements include a promoter that may be isolated from any gene of eukaryotic or viral origin. Although the E3 genes can be controled by the homologous E3 promoter, it is preferred use a heterologous promoter (regulatable or constitutive) that may be chosen among those cited previously, the immediate early promoter of the CMV being preferred. The person skilled in the art is capable to link said polynucleotide to an appropriate promoter in an operative way. When the polynucleotide comprises several E3 genes, these may be expressed from a unique promoter or independent ones. In this case, the different E3 cassettes may be in the same or opposite direction and in the same and different locations within one or more vector(s). However, the use of a unique promoter to drive transcription of the selected E3 sequences is preferred, especially in the case where the polynucleotide encodes both a functional 14.5K protein and a functional 10.4K protein. In with context, it is advantageous to have the 10.4K encoding sequences preceding the 14.5K encoding sequences and the stop codon of the 10.4K protein being separated by 2 bp from the start codon of the 14.5K protein, as found in the wild type context.

In order to stabilize expression, it may be advantageous that the E3 gene(s) retain or comprise splicing sequences. They may be homologous (derived from E3 sequences) or heterologous (derived from any eukaryotic gene or from synthetic origin). The large variety of splicing sequences described in the state of the art are suitable in the context of the invention, including those previously cited.

Advantageously, the polynucleotide in use in the present invention is inserted in an expression vector. Such an expression vector can further comprise a gene of interest operably linked to the regulatory elements allowing its expression in a host cell. With respect to the nature of the gene of interest and the regulatory regions, the same applies as already set forth in connection with the adenoviral vectors according to the invention.

In the context of the present invention, the expression vector can be a plasmid or a viral vector. In the preferred embodiment according to which the polynucleotide and gene of interest are inserted into the same expression vector, they may be inserted in the same location (i.e., in place of the deleted E1 sequences in an E1⁻ adenoviral vector) or at different locations (e.g., the gene of interest in place of the deleted E1 sequences and the polynucleotide in place of the native E3 region or vice versa). The use of two independent expression vectors each carrying said polynucleotide and gene of interest is also feasible. In this case, both vectors may be introduced in the host cell, tissue or organism together (co-transfection or co-infection) or separately. Preferably the vector carrying the polynucleotide is injected prior the vector carrying the gene of interest, especially when this latter is susceptible to induce an inflammatory condition.

The term "plasmid" denotes an extrachromosomal circular DNA capable of autonomous replication in a given cell. The range of suitable plasmids is very large. Preferably, the plasmid is designed for amplification in bacteria and for expression in an eukaryotic target cell. Such plasmids can be purchased from a variety of manufacturers. Suitable plasmids include but are not limited to those derived from pBR322 (Gibco BRL), pUC (Gibco BRL), pBluescript (Stratagene), pREP4, pCEP4 (Invitrogene), pCI (Promega) and p Poly (Lathe et al., Gene 57 (1987), 193–201). It can also be engineered by standard molecular biology techniques (Sambrook et al., Laboratory Manual, Cold Spring Harbor Laboratory Press, Cold Spring Harbor (1989), N.Y.). It may also comprise a selection gene in order to select or to identify the transfected cells (e.g., by complementation of a cell auxotrophy or by antibiotic resistance), stabilizing elements (e.g., cer sequence; Summers and Sherrat, 1984, Cell 36, 1097–1103) or integrative elements (e.g., LTR viral sequences and transposons).

A preferred embodiment relates to the use of a viral vector derived from a virus selected from the group consisting of herpes viruses, cytomegaloviruses, foamy viruses, lentiviruses, Semliki forrest virus, AAV (adeno-associated virus), poxviruses, adenoviruses and retroviruses. Such viral vectors are well known in the art. "Derived" means genetically engineered from the native viral genome by introducing one or more modifications, such as deletion(s), addition(s) and/or substitution(s) of one or several nucleotide(s) present in a coding or a non-coding portion of the viral genome.

A viral vector which is particularly appropriate for the present invention is an adenoviral vector. With respect to the nature and structure of the adenoviral vector, the location of the inserted E3 genes and the regulatory regions, the same applies as already set forth in connection with the adenoviral vectors according to the invention.

The polynucleotide in use in the present invention can be inserted in any location of the adenoviral genome, with the exception of the cis-acting sequences. Preferably, said adenoviral vector is derived from an adenovirus genome in which all or part of the E1 region and all of the native E3 region are deleted or non functional. Furthermore, the adenoviral backbone may comprise additional modifications. A particular embodiment encompasses the use of an adenoviral vector in which one or more viral gene(s) of the E2, E4 and/or L1–L5 region(s) is (are) further deleted or non functional (illustrative examples of such modifications are cited above). As mentioned before, adenoviruses adaptable for use in accordance with the present invention, can be derived from any human or animal source and any serotype can be employed, with a special preference for adenoviruses 2 (Ad2) and 5 (Ad5). The present invention encompasses the use of an adenoviral vector derived from the genome of a particular adenovirus (i.e., human adenovirus 5) and a polynucleotide carrying E3 gene(s) isolated from the genome of another adenovirus (i.e., human adenovirus 2)

The E3 gene(s) in use in the present invention is (are) inserted in replacement of a deleted region, with a special preference for the deleted E1 and/or E3 region and positioned in sense or anti-sense orientation relative to the transcriptional direction of the region in question. Preferably, when the polynucleotide encodes a functional 14.7K protein, it is inserted in the adenoviral vector either (i) at a location where the E3 region normally resides and in anti-sense orientation relative to the transcriptional direction of the native E3 region or (ii) where the E1 region normally resides and in sense orientation relative to the transcriptional direction of the native E1 region. Referring to the embodiment where the polynucleotide encodes a functional 14.5K protein and a functional 10.4K protein, said polynucleotide is preferably inserted in the adenoviral vector at a location where the E3 region normally resides and in sense orientation relative to the transcriptional direction of the native E3 region.

In addition, adenoviral particles or empty adenoviral capsids can also be used to transfer nucleic acids (e.g., a plasmidic vector) by a virus-mediated co-internalization process as described in U.S. Pat. No. 5,928,944. This process can be accomplished in the presence of (a) cationic agent(s) such as polycarbenes or lipid vesicles comprising one or more lipid layers.

A retroviral vector is also suitable. Retroviruses are a class of integrative viruses which replicate using a virus-encoded reverse transcriptase, to replicate the viral RNA genome into double stranded DNA which is integrated into chromosomal DNA of the infected host cells. The numerous vectors described in the literature may be used within the framework of the present invention and especially those derived from murine leukemia viruses, especially Moloney (Gilboa et al., 1988, Adv. Exp. Med. Biol. 241, 29) or Friend's FB29 strains (WO95/01447). Generally, a retroviral vector is deleted of all or part of the viral genes gag, pol and env and retains 5' and 3' LTRs and an encapsidation sequence. These elements may be modified to increase expression level or stability of the retroviral vector. Such modifications include the replacement of the retroviral encapsidation sequence by one of a retrotransposon such as VL30 (U.S. Pat. No. 5,747,323). The gene of interest is generally placed under the control of a non-retroviral promoter and the resulting cassette is inserted downstream of the encapsidation sequence, preferably in anti-sense orientation relative to the transcriptional direction of the retroviral genome.

Poxviruses are a group of complex enveloped viruses that distinguish from the above-mentioned viruses by their large DNA genome and their cytoplasmic site of replication. The genome of several members of poxviridae has been mapped and sequenced. It is a double-stranded DNA of approximately 200 kb coding for about 200 proteins of which approximately 100 are involved in virus assembly. In the context of the present invention, a poxviral vector may be obtained from any member of the poxviridae, in particular canarypox, fowlpox and vaccinia virus, the latter being preferred. Suitable vaccinia viruses include without limitation the Copenhagen strain (Goebel et al., 1990, Virol. 179, 247–266 and 517–563; Johnson et al., 1993, Virol. 196, 381–401), the Wyeth strain and the modified Ankara (MVA) strain (Antoine et al., 1998, Virol. 244, 365–396). The general conditions for constructing a vaccinia virus comprising one or more gene(s) of an adenoviral E3 region and, optionally a gene of interest, are well known in the art (see for example EP 83 286 and EP 206 920 for Copenhagen vaccinia viruses and Mayr et al., 1975, Infection 3, 6–14 and Sutter and Moss, 1992, Proc. Natl. Acad. Sci. USA 89, 10847–10851 for MVA viruses).

The E3 gene(s) and the gene of interest are preferably inserted within the poxviral genome in a non-essential locus, such as non-coding intergenic regions or any poxviral gene for which inactivation or deletion does not significantly impair viral growth and replication. Thymidine kinase gene is particularly appropriate for insertion in Copenhagen vaccinia viruses (Hruby et al., 1983, Proc. Natl. Acad. Sci USA 80, 3411–3415; Weir et al., 1983, J. Virol. 46, 530–537). As far as MVA is concerned, insertion of the expression cassette can be performed in any of the excisions I to VII, and preferably in excision II or III (Meyer et al., 1991, J. Gen. Virol. 72, 1031–1038; Sutter et al., 1994, Vaccine 12, 1032–1040) or in D4R locus. For fowlpox virus, insertion within thymidine kinase gene and/or a non-coding intergenic region may be considered (see for example EP 314 569 and U.S. Pat. No. 5,180,675). One may also envisage insertion in an essential viral locus provided that the defective function be supplied in trans, via a helper virus or by expression in the producer cell line.

According to an advantageous alternative, a viral or especially a non viral (i.e., plasmid) vector used in the present invention may be complexed to lipids and/or polymers (synthetic vector). Preferred lipids are cationic lipids which have a high affinity for nucleic acids and which interact with cell membranes (Felgner et al., 1989, Nature 337, 387–388). As a result, they capable of forming a complex with the nucleic acid, thus generating a compact particle capable of entering the cells. Suitable lipids include without limitation DOTMA (Felgner et al., 1987, Proc. Natl. Acad. Sci. USA 84, 7413–7417), DOGS or Transfectam™ (Behr et al., 1989, Proc. Natl. Acad. Sci. USA 86, 6982–6986), DMRIE or DORIE (Felgner et al., 1993, Methods 5, 67–75), DC-CHOL (Gao and Huang, 1991, BBRC 179, 280–285), DOTAP™ (McLachlan et al., 1995, Gene Therapy 2, 674–622), Lipofectamine™ and glycerolipid compounds (see EP901463 and WO98/37916).

Suitable polymers are preferably cationic, such as polyamidoamine (Haensler and Szoka, 1993, Bioconjugate Chem. 4, 372–379), dendritic polymer (WO 95/24221), polyethylene imine or polypropylene imine (WO 96/02655), polylysine (U.S. Pat. No. 5,595,897 or FR 2 719 316), chitosan (U.S. Pat. No. 5,744,166) or DEAE dextran (Lopata et al., 1984, Nucleic Acid Res. 12, 5707–5717).

The present invention also relates to a method for preparing a viral particle, comprising:

(i) introducing the adenoviral vector of the invention or the viral expression vector described in connection with use according to the present invention into a permissive cell, to obtain a transfected permissive cell;

(ii) culturing said transfected permissive cell for an appropriate period of time and under suitable conditions to allow the production of said viral particle;

(iii) recovering said viral particle from the cell culture; and (iv) optionally purifying the recovered viral particle.

The vector can be introduced into the permissive cell by any one of a variety of methods known in the art. One may proceed by transfection of the vector or fragments thereof, by lipofection, electroporation and/or by infection. The permissive cell is preferably a complementing cell, which provides in trans all gene products necessary to produce infectious viral particles. The virions may be recovered from the culture supernatant but also from the cells which can be lysed by chemical, mechanical or any other means (for example, by a series of thawing/freezing cycles). Optionally, the virions may be amplified and purified according to standard techniques (chromatography, ultracentrifugation, for example in a cesium chloride gradient . . . ).

In a further embodiment, the present invention also relates to a viral particle comprising an adenoviral vector according to the invention or a viral expression vector as described in connection with the use according to the invention.

Adenoviral particles can be prepared according to any conventional technique in the field of the art, such as homologous recombination in a permissive cell line (e.g., as described in Graham and Prevect, 1991, Methods in Molecular Biology, Vol 7, Gene Transfer and Expression Protocols; Ed E. J. Murray, The Human Press Inc, Clinton, N.J.) or in *Escherichia coli* (as described in WO96/17070). Propagation is advantageously performed in a complementing cell line or in the presence of a helper virus providing complementation in trans. "Complementing" or "complementation" denotes that the capability to encode and/or express functions that are defective in the vector but necessary for generating viable viral particles. The cell lines 293 (Graham et al., 1977, J. Gen. Virol. 36, 59–72) and PERC6 (Fallaux et al., 1998, Human Gene Therapy 9, 1909–1917) are commonly used to complement the E1 function. Other cell lines have been engineered to complement doubly defective vectors (Yeh et al., 1996, J. Virol. 70, 559–565; Krougliak and Graham, 1995, Human Gene Ther. 6, 1575–1586; Wang et al., 1995, Gene Ther. 2, 775–783; Lusky et al., 1998, J. Virol. 72, 2022–2033; EP919627 and WO97/04119). The adenoviral particles can be recovered from the culture supernatant but also from the cells after lysis and optionally further purified according to standard techniques (e.g., chromatography, ultracentrifugation, as described in WO96/27677, WO98/00524 and WO98/26048). Furthermore, the virions may be amplified by successive passage in a permissive cell in order to generate a high titer viral stock that may be used in the preparation of clinical lots Retroviral particles are prepared in the presence of a helper virus or in an appropriate complementation (packaging) cell line which contains integrated into its genome the retroviral genes for which the retroviral vector is defective (e.g., gag/pol and env). Such cell lines are described in the prior art (Miller and Rosman, 1989, Bio-Techniques 7, 980; Danos and Mulligan, 1988, Proc. Natl. Acad. Sci. USA 85, 6460; Markowitz et al., 1988, Virol. 167, 400). The product of the env gene is responsible for the binding of the viral particle to the viral receptor present on the surface of the target cell and, therefore determines the host range of the retroviral particle. In the context of the invention, it is advantageous to use a packaging cell line, such as the PA317 cells (ATCC CRL 9078) or 293E16

(WO97/35996) containing an amphotropic envelope protein, to allow infection of human and other species' host cells. The retroviral particles are preferably recovered from the culture supernatant and may optionally be further purified according to standard techniques (e.g., chromatography, ultracentrifugation).

Poxviral particles are prepared as described in numerous documents accessible to the artisan skilled in the art (Piccini et al., 1987, Methods of Enzymology 153, 545–563; U.S. Pat. Nos. 4,769,330; 4,772,848; 4,603,112; 5,100,587 and 5,179,993). The major techniques that have been developed utilize homologous recombination between a donor plasmid containing the gene to be inserted (e.g., polynucleotide and/or gene of interest) and the wild type poxviral genome. Generally, the donor plasmid is constructed, amplified in $E.\ coli$ and isolated by conventional procedures. Then, it is introduced into a suitable cell culture (e.g., chicken embryo fibroblasts) together with a poxvirus genome, to produce by homologous recombination the poxviral particles of the invention. They can be recovered from the culture supernatant or from the cultured cells after a lysis step (chemical, freezing/thawing, osmotic shock, mechanic shock, sonication and the like) and can be, if necessary, isolated from wild type contamination by consecutive rounds of plaque purification and then purified using the techniques of the art (chromatographic methods, ultracentrifugation on cesium chloride or sucrose gradient).

The present invention also encompasses vectors or particles that have been modified to allow preferential targeting of a particular target cell. A characteristic feature of targeted vectors/particles of the invention (of both viral and non-viral origins, such as polymer- and lipid-complexed vectors) is the presence at their surface of a targeting moiety capable of recognizing and binding to a cellular and surface-exposed component. Such targeting moieties include without limitation chemical conjugates, lipids, glycolipids, hormones, sugars, polymers (e.g., PEG, polylysine, PEI and the like), peptides, polypeptides (for example JTS1 as described in WO 94/40958), oligonucleotides, vitamins, antigens, lectins, antibodies and fragments thereof. They are preferably capable of recognizing and binding to cell-specific markers, tissue-specific markers, cellular receptors, viral antigens, antigenic epitopes or tumor-associated markers.

Cell type-specific targeting may be achieved with vectors derived from viruses having a broad host range by the modification of viral surface proteins. For example, the specificity of infection of adenoviruses is determined by the attachment to cellular receptors present at the surface of permissive cells. In this regard, the fiber and penton present at the surface of the adenoviral capsid play a critical role in cellular attachment (Defer et al. J. Virol. 64 (1990) 3661–3673). Thus, cell targeting of adenoviruses can be carried out by genetic modification of the viral gene encoding fiber and/or penton, to generate modified fiber and/or penton capable of specific interaction with unique cell surface polypeptides. Examples of such modifications are described in literature (for example in Wickam et al., 1997, J. Virol. 71, 8221–8229; Arnberg et al., 1997, Virol. 227, 239–244; Michael et al., 1995, Gene Therapy 2, 660–668; WO94/10323). To illustrate, inserting a sequence coding for EGF within the sequence encoding the adenoviral fiber will allow to target EGF receptor expressing cells.

Other methods for cell specific targeting have been achieved by the conjugation of antibodies or antibody fragments to the retroviral envelope protein (Michael et al., 1993, J. Biol. Chem 268, 6866–6869; Roux et al., 1989, Proc. Natl. Acad Sci. USA 86, 9079–9083; Miller and Vile, 1995, FASEB J. 9, 190–199 and WO93/09221) and of polypeptides having a nucleic acid binding domain and a targeting moiety (WO95/28494).

The present invention also provides a host cell comprising an adenoviral vector of the invention, a polynucleotide or an expression vector as defined in connection with the use of the invention or infected by a viral particle of the invention. The vector may be inserted into the cellular genome or not (episome). A host cell may be unique type of cells or a group of different types of cells and encompass cultured cell lines, primary cells and proliferative cells, with a special preference for cells of human origin. Preferred host cells include fibroblasts, muscle cells (such as cardiomyocytes, myofibroblasts, satellite cells, myocytes, myoblastes, smooth muscle cells especially of the arterial system and, particularly, of the vascular system), haematopoïetic (totipotent stem cells, leucocytes, lymphocytes, monocytes, macrophages . . . ), lung, tracheal, liver, epithelial and endothelial cells.

The present invention also relates to a composition, preferably a pharmaceutical composition, comprising as an agent an adenoviral vector according to the invention, a polynucleotide or an expression vector as described in connection with the use of the invention, a host cell or a viral particle according to the invention or prepared according to the method of the invention. In a special case, the composition may comprise two or more E3 genes, vectors, viral particles or eukaryotic host cells, which may differ by the nature (i) of said E3 genes and/or (ii) of the regulatory elements providing their expression in the host cell and/or (iii) of the gene of interest eventually carried by the vector and/or (iv) of the vector backbone.

The composition according to the invention may be manufactured in a conventional manner for a variety of modes of administration including systemic, topical and local administration. Referring to systemic administration, injection is preferred, e.g., intravenous, intraperitoneal, intragastric, subcutaneous, intracardiac, intraarterial, intracoronary, intravascular, intraarterial, intramuscular, intrathecal, intratumoral, intranasal, intrapulmonary or intratracheal routes. Local administration include aerosolization instillation and oral routes of administration. The administration may take place in a single dose or a dose repeated one or several times after a certain time interval. The appropriate administration route and dosage vary in accordance with various parameters, for example, with the individual, the condition or disease to be treated, the stage to which it has progressed, the need for prevention or therapy and the gene of interest to be transferred. As an indication, a composition based on viral particles may be formulated in the form of doses of between $10^4$ and $10^{14}$ iu (infectious unit), advantageously between $10^5$ and $10^{13}$ iu and preferably between $10^6$ and $10^{12}$ iu. The titer may be determined by conventional techniques (see for example Lusky et al., 1998, supra). The doses of DNA vector are preferably comprised between 0.01 and 10 mg/kg, and more especially between 0.5 and 2 mg/kg. The composition of the invention can be in various forms, e.g., solid (powder, lyophilized form) or liquid (e.g., aqueous).

In a preferred embodiment, the composition comprises a pharmaceutically acceptable carrier, allowing its use in a method for the therapeutic treatment of humans or animals. In this particular case, the carrier is preferably a pharmaceutically suitable injectable carrier or diluent which is non-toxic to a human or animal organism at the dosage and concentration employed (for examples, see Remington's Pharmaceutical Sciences, $16^{th}$ ed. 1980, Mack Publishing Co). It is preferably isotonic, hypotonic or weakly hypertonic and has a relatively low ionic strength, such as provided by a sucrose solution. Furthermore, it may contain any relevant solvents, aqueous or partly aqueous liquid carriers comprising sterile, pyrogen-free water, dispersion media, coatings, and equivalents, or diluents (e.g., Tris-HCl, acetate, phosphate), emulsifiers, solubilizers, excipients or adjuvants. The pH of the composition is suitably adjusted and buffered in order to be appropriate for use in humans or animals. Representative examples of carriers or diluents for an injectable composition include water, isotonic saline solutions which are preferably buffered at a physiological pH (such as phosphate buffered saline, Tris buffered saline, mannitol, dextrose, glycerol containing or not polypeptides or proteins such as human serum albumin). For example, such a composition may comprise 10 mg/ml mannitol, 1 mg/ml HSA, 20 mM Tris pH 7.2 and 150 mM NaCl.

In addition, the composition according to the present invention may include one or more stabilizing substance(s), such as lipids (e.g., cationic lipids, liposomes, lipids as described in WO98/44143; Felgner et al., 1987, Proc. West. Pharmacol. Soc. 32, 115–121; Hodgson and Solaiman, 1996, Nature Biotechnology 14, 339–342; Remy et al., 1994, Bioconjugate Chemistry 5, 647–654), nuclease inhibitors, hydrogel, hyaluronidase (WO98/53853), collagenase, polymers, chelating agents (EP890362), in order to preserve its degradation within the animal/human body and/or improve delivery into the host cell. Such substances may be used alone or in combination (e.g., cationic and neutral lipids). It may also comprise substances susceptible to facilitate gene transfer for special applications, such as a gel complex of polylysine and lactose facilitating delivery by intraarterial route (Midoux et al., 1993, Nucleic Acid Res. 21, 871–878) or poloxamer 407 (Pastore, 1994, Circulation 90, I-517). It has also be shown that adenovirus proteins are capable of destabilizing endosomes and enhancing the uptake of DNA into cells. The mixture of adenoviruses to solutions containing a lipid-complexed plasmid vector or the binding of DNA to polylysine covalently attached to adenoviruses using protein cross-linking agents may substantially improve the uptake and expression of the vector (Curiel et al., 1992, Am. J. Respir. Cell. Mol. Biol. 6, 247–252).

The composition of the present invention is particularly intended for the protection (preventive or curative) from an inflammatory condition, such as septic shock, fulminant hepatic failure, hepatitis (especially hepatitis B and C), cirrhosis, alcoholic liver diseases, chemotherapy-induced toxicity, graft rejection, immune disorders (e.g., chronic inflammation or autoimmunity), neoplastic diseases (e.g., tumors and tumor metastasis) and connective tissue disorders (e.g., rheumatoid arthritis, atherosclerosis).

A preferred application is the protection from an inflammation condition associated with the administration of a gene therapy vector. Administration of conventional gene-therapy vectors may be associated with acute inflammation and toxicity in the treated organism, which result in the elimination of the infected cells from said organism and rapid loss of gene expression. The adenoviral vector or the polynucleotide and expression vector of the invention may at least partially protect from such inflammation condition and/or toxicity and, thus, allow prolonged gene expression. Gene expression can be determined by evaluating the level of the gene product over time, either in vitro (e.g., in cultured cells) or in vivo (e.g., in animal models), by standard methods such as flow cytofluorimetry, ELISA, immunofluorescence, Western blotting, biological activity measurement and the like. The improvement of gene expression compared to a control not containing or not expressing the E3 gene(s) carried by the adenoviral vector, polynucleotide of the invention can be seen in terms of the amount of gene product or in terms of the persistence of the expression (stability over a longer period of time).

The present invention also provides the use of an adenoviral vector according to the invention, a polynucleotide or an expression vector, as described in connection with the use according to the invention, a viral particle or a host cell according to the invention for the preparation of a medicament intended for gene transfer, preferably into a human or animal body. Within the scope of the present invention, "gene transfer" has to be understood as a method for introducing any gene of interest into a cell. Thus, it also includes immunotherapy that relates to the introduction of a potentially antigenic epitope into a cell to induce an immune response which can be cellular or humoral or both.

For this purpose, the adenoviral vector, the polynucleotide and expression vector or the viral particle of the present invention may be delivered in vivo to the human or animal organism by specific delivery means adapted to the pathology to be treated. For example, a balloon catheter or a stent coated with the adenoviral vector, the expression vector carrying the polynucleotide or the viral particle may be employed to efficiently reach the cardiovascular system (as described in Riessen et al., 1993, Hum Gene Ther. 4, 749–758; Feldman and Steg, 1996, Medecine/Science 12, 47–55). It is also possible to deliver said therapeutic agents by direct administration, e.g., intravenously, in an accessible tumor, in the lungs by aerosolization and the like. Alternatively, one may employ eukaryotic host cells that have been engineered ex vivo to contain the adenoviral vector, the expression vector carrying the polynucleotide or the viral particle according to the invention. Methods for introducing such elements into an eukaryotic cell are well known to those skilled in the art and include microinjection of minute amounts of DNA into the nucleus of a cell (Capechi et al., 1980, Cell 22, 479–488), transfection with $CaPO_4$ (Chen and Okayama, 1987, Mol. Cell Biol. 7, 2745–2752), electroporation (Chu et al., 1987, Nucleic Acid Res. 15, 1311–1326), lipofection/liposome fusion (Felgner et al., 1987, Proc. Natl. Acad. Sci. USA 84, 7413–7417) and particle bombardement (Yang et al., 1990, Proc. Natl. Acad. Sci. USA 87, 9568–9572). The graft of engineered cells is also possible in the context of the present invention (Lynch et al, 1992, Proc. Natl. Acad. Sci. USA 89, 1138–1142).

The present invention also provides the use of the adenoviral vector of the invention, of the polynucleotide or the expression vector as described in connection with the use of the present invention, of the viral particle, or the host cell of the invention, for the preparation of a medicament intended for the treatment or the prevention of an inflammatory condition. With respect to the administration routes, the same applies as already set forth in connection with the use for gene transfer.

In a first preferred embodiment of said use of the present invention, the inflammatory condition is mediated by TNF, and more especially, TNFα. The E3 gene preferably used in this context encodes a functional 14.7K protein.

In a second preferred embodiment of said use of the present invention, the inflammatory condition is mediated by Fas. The E3 genes preferably used in this context encode functional 10.4K and 14.5K proteins, (preferably associated as a complex, e.g., the so-called RID complex).

In a third preferred embodiment of said use of the present invention, the inflammatory condition is mediated by a gene therapy vector, e.g., by the viral gene product(s) of a viral gene therapy vector and/or by the expression product of a gene of interest. The E3 gene(s) preferably used in this context encode(s) a functional 14.7K, 10.4K or 14.5K protein, taken individually or in combination.

The present invention also relates to a method for the treatment of a human or animal organism, comprising administering to said organism a therapeutically effective amount of an adenoviral vector of the invention, the polynucleotide or expression vector as described in connection with the use according to the invention, a viral particle or an eukaryotic cell according to the invention.

A "therapeutically effective amount" is a dose sufficient for the alleviation of one or more symptoms normally associated with the disease or condition desired to be treated. When prophylactic use is concerned, this term means a dose sufficient to prevent or to delay the establishment of a disease or condition.

The method of the present invention can be used for preventive purposes and for therapeutic applications relative to the diseases or conditions listed above. The present method is particularly useful to prevent or reduce the establishment of an inflammatory response following administration of a conventional gene-therapy vector. It is to be understood that the present method can be carried out by any of a variety of approaches. Advantageously, the vector, viral particle, cell or the pharmaceutical composition of the invention can be administered directly in vivo by any conventional and physiologically acceptable administration route, for example by intravenous injection, by direct injection into an accessible tumor or by means of an appropriate catheter into the vascular system, etc. Alternatively, the ex vivo approach may also be adopted which consists of introducing the adenoviral vector, the polynucleotide or the viral particle according to the invention into cells, growing the transfected/infected cells in vitro and then reintroducing them into the patient to be treated.

In order to improve gene transfer, the patient may undergo a macrophage depletion treatment prior to administration of the composition of the invention. Such a technique is described in literature (for example in Van Rooijen et al., 1997, TibTech, 15, 178–184).

When the method of the invention uses a gene-therapy vector engineered to express a suicide gene, it can be advantageous to additionally administer a pharmaceutically acceptable quantity of a prodrug which is specific for the expressed suicide gene product. The two administrations can be made simultaneously or consecutively, but preferably the prodrug is administered after the composition of the invention. By way of illustration, it is possible to use a dose of prodrug from 50 to 500 mg/kg/day, a dose of 200 mg/kg/day being preferred. The prodrug is administered in accordance with standard practice. The oral route is preferred. It is possible to administer a single dose of prodrug or doses which are repeated for a time sufficiently long to enable the toxic metabolite to be produced within the host organism or the target cell. As mentioned above, the prodrug ganciclovir or acyclovir can be used in combination with the TK HSV-1 gene product and 5-FC in combination with the cytosine deaminase and/or uracil phosphotransferase gene product.

Prevention or treatment of a disease or a condition can be carried out using the present method alone or, if desired, in conjunction with presently available methods (e.g., radiation, chemotherapy and surgery such as angioplasty).

The present invention also relates to the use of (an) expression product(s) encoded by the E3 gene(s) used in the context of the present invention, to protect a host cell, tissue or organism from an inflammatory condition. The anti-inflammatory protective effect has been defined previously. The present invention encompases the use of the native E3 expression product as found in an adenovirus-infected cell, a fragment thereof or a modified variant, provided that the anti-inflammatory function be preserved.

The expression product(s) of the E3 gene(s) can be produced by the conventional methods of chemical synthesis or alternatively by recombinant DNA techniques (see for example Maniatis et al, 1989, Laboratory Manual, Cold Spring Harbor, N.Y.). More particularly, a method of preparation comprises the act of culturing a cell transfected the E3 gene(s) coding for the expression product(s) in question so as to generate a producing cell and the act of harvesting said expression product(s) from the cell culture. The producing cell may be of any origin and without limitation a bacterium, a yeast or a mammalian cell, the E3 gene(s) considered being either integriated into the cellular genome or integrated into an appropriate expression vector. Of course, the E3 gene(s) is (are) placed under the control of transcriptional and translational signals allowing its (their) expression in the producing cell. Expression vectors and control signals are known to the person skilled in the art and examples have been illustrated above.

The present invention also relates to a composition comprising such expression product(s) and its use for the preparation of a drug intended for the treatment or the prevention of an inflammatory condition. The expression product of an E3 gene encoding a functional 14.7K protein is preferably used for the preparation of a drug intended for the treatment or the prevention of a TNF-mediated inflammatory condition whereas the expression products of E3 genes encoding both functional 14.5K and 10.4K proteins are preferably used for the preparation of a drug intended for the treatment or the prevention of a Fas-mediated inflammatory condition. The expression product(s) of E3 gene(s) encoding either a functional 14.7K protein or both functional 14.5K and 10.4K proteins or functional 14.7K, 14.5K and 10.4K proteins is (are) preferably used for the preparation of a drug intended for the treatment or the prevention of an inflammatory condition mediated by a gene therapy vector.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practiced in a different way from what is specifically described herein.

All of the above cited disclosures of patents, publications and database entries are specifically incorporated herein by reference in their entirety to the same extent as if each such individual patent, publication or entry were specifically and individually indicated to be incorporated by reference.

The following examples serve to illustrate the present invention.

EXAMPLES

Plasmids and Viral Vectors

The adenoviral genome fragments employed in the different constructs described below are given precisely in accordance with their positions in the nucleotide sequence of the Ad5 genome, as disclosed in Chroboczek et al. (1992, Virol. 186, 280–285).

Standard cloning methods (Sambrook et al., 1989, Laboratory Manual, Cold Spring Harbor Laboratory Press, Cold Spring Harbor N.Y.) were used to generate the following vectors.

The genomes of all viral vectors were generated by homologous recombination between a transfer plasmid and a linearized plasmid containing the viral backbone as described in Chartier et al. (1996, J. Virol.70, 4805–4810). Briefly, vectors are deleted in the E1 region between nucleotides 459 and 3327 and in the E3 region between nucleotides 28249 to 30758.

The 14.7K expression cassette is made of the cytomegalovirus immediate early promoter (Boshart et al., 1985, Cell 41, 521–530), a chimeric intron (as found in pCI vector available in Promega made of the human β-globin donor fused to the immunoglobulin gene acceptor) and the SV40 polyadenylation sequence into which the 14.7K DNA fragment was cloned (nucleotides 30453 to 30836 of the Ad5 genome). The 14.7 ORF was amplified by PCR with oligonucleotides that contained AatII sites at their extremities which allowed cloning in the AatII site of the polylinker of the expression cassette (5' oligonucleotide: 5'-TACGACGTCATGACTGACACCCTAGATCTAGAAA TGGA-3' (SEQ ID NO: 1) and 3' oligonucleotide: 5'-CATGACGTCTACGTATTAGTTAAAGGGAATAAGAT CTTTGAG-3' (SEQ ID NO: 2). After sequencing, the product of amplification was subcloned in the transfer plasmids. The 14.7K expression cassette was flanked by adenovirus sequences required for transfer in the viral genome plasmid: Nucleotides 1–458 and 3328–5788 for homologous recombination in the E1 region and nucleotides 21638–21562 and 30758–35935 for homologous recombination in the E3 region.

The RID complex expressing vectors were obtained by using the same transfer vectors described above except that the AflIII-XbaI fragment, spanning the 10.4–14.5 genes (nucleotides 29748–30470) was cloned in place of the 14.7K gene.

Virus Generation, Viral Growth, and Titration.

Viruses were generated by releasing the viral genomes from the recombinant plasmids by PacI digestion and transfecting them into the appropriate complementation cell lines. Virus propagation, purification, and titration of infectious units (IU) by indirect immunofluorescence of the viral DNA binding protein (DBP) were carried out as described previously (Lusky et al., 1998, J. Virol 72, 2022–2032). Purified virus was stored in viral storage buffer (1 M sucrose, 10 mM Tris-HCl [pH 8.5], 1 mM MgCl2, 150 mM NaCl, 0.005% [vol/vol] Tween 80).

In vitro TNFα-induced Apoptosis Inhibition Assay

To test if vectors with the 14.7K expression cassette were functional in vitro, $10^4$ A549 cells (human lung carcinoma ATCC CCL-185), Hela cells (ATCC CCL-2) or the mouse fibroblast line C3H (Reznikoff et al., 1973, Cancer Res. 33, 3231–3238) were plated per well of a 96 well plate. 24 hours later, cells were infected at the indicated multiplicity of infection (MOI) either with wild type adenovirus serotype 5, E1-deleted E3-deleted (E1°E3°) vector or 14.7K-constitutive vectors. Next day, virus was removed and half the wells were exposed to cycloheximine (25 μg/ml) and TNFα (500 units/ml; Valbiotech) or cycloheximine alone in DMEM without phenol-red (Sigma) supplemented with dialyzed and heat inactivated fetal calf serum. 16 hours later, 50 μl of supernatant was sampled from each well and its content in lactate dehydrogenase was determined using the Cytotox96 test (Promega). OD values used in calculations are means of triplicates. Results are expressed a % specific lysis and were calculated with the following formula % specific lysis=(OD value of sample−OD value of spontaneous release)/(OD value of 100% lysis−OD value of spontaneous release). Background OD value was subtracted from each value prior to calculation.

Down-modulation of the EGFR from the Cell Surface

Down modulation of the EGF receptor from the surface of the infected cells was measured by cytofluorometry. Mock-infected A549 cells or cells infected either with a control vector (E1–E3–) or with a RID constitutive vector were detached from the culture vessel with a 10 mM EDTA solution in PBS. $2\times10^5$ cells from each population was exposed to an FITC-conjugated anti-EGFR antiboby (Novus Molecular Inc, San Diego Calif.) (10 μg/ml; total volume added 50 μl) for 10 min on ice. Cells were washed twice and levels of fluorescence determined using a Facsan (Becton Dickenson).

Animal Studies

Six-week-old female Balb/C were purchased from IFFA-CREDO (L'Arbreles, France). For intravenous injections, the volume of vector corresponding to the indicated amount was diluted in storage buffer so that each mouse received the viral dose in a final volume of 200 ml. For intratracheal injections, the volume of virus corresponding to the desired viral dose was diluted in 0.9% NaCl. Animals were sacrificed at the times indicated, and organs were removed, cut into equal pieces, immediately frozen in liquid nitrogen until analysis or fixed in 4% formaldehyde for pathological analysis or detection of apoptosis.

To induce acute hepatitis, each animal received intraperitonially on the left side, 25 mg of D(+)galactosamine (Sigma; G1639) in 100 ml of PBS followed by 300 ng of LPS (Sigma; L3137) in 100 ml of PBS. Alternatively, each animal was injected intravenously with 6 mg of anti-Fas antibody (Pharmingen 15400D) in a total volume of 200 ml of PBS. Mortality was monitored every 3 hours the first day and daily from the second day on.

Nucleic Acid Analysis

For total DNA extraction tissues were digested overnight with a proteinase K solution (1 mg of proteinase K in 1% sodium dodecyl sulfate (SDS), 10 mM Tris-HCl (pH 7.4, 400 mM NaCl, 2 mM EDTA). Total cellular DNA was isolated by phenol-chloroform extraction followed by ethanol precipitation. DNA (10 μg) was digested with HindIII and analyzed by southern blot analysis using a $^{32}$P-labeled HindIII restriction fragment purified from Ad5 genomic DNA (nt 18318 to 26328). The quality and quantities of DNA were monitored by ethidium bromide staining of the gels prior to transfer.

Gene expression was monitored by Northern blot analysis. To this end, total RNA was extracted from organs by using the RNA Now kit (Ozyme, Saint-Quentin-les-Yvelines, France) as recommended by the supplier. Ten μg of total RNA was subjected to agarose gel electrophoresis and transferred to nitrocellulose filters. Filters were stained after transfer to ensure that equal amounts of total cellular RNA were loaded and transferred. The 14.7-specific mRNA was detected by using a $^{32}$P-labeled oligonucleotide (5' AGGTGAGTGAATGCAGCCTTCGGT 3'; SEQ ID NO: 3). The RID complex-specific mRNA was detected by using a $^{32}$P-labeled oligonucleotide (5' AGTGATGAGGCTGCA-GATGAGCGTGA 3'; SEQ ID NO: 4).

In situ Cell Death Assay

Organs fixed in 4% formaldehyde at time of sampling were dehydrated using ethanol of increasing strength and embedded in paraffin. Six μm thick sections were deparaffinized in xylene and rehydrated in PBS. Slides were treated with proteinase K (10 mg/ml) for 10 minutes at 37° C. and permeabilized by a Triton-X treatment (0.1% in PBS) for 2 minutes on ice. Apoptotic cells were revealed with the In situ cell death detection kit (Boehringer Mannheim) as described by the manufacturer. Slides were counterstained with methyl green and mounted in permount (Baker).

Example 1

Functionality of RID-expressing Adenoviral Vectors

A. In vitro Functionality of Adenoviral Vectors Constitutively Expressing the RID Complex Two types of RIDab-constitutive vectors were designed. The first series made use of the cDNA of each protein separated by an IRES in a 10.4K-IRES-14.5K type organization. This construct was placed in an expression cassette made of the cytomegalovirus immediate early promoter (CMVp) a chimeric intron (intron of pCI vector made of the human β-globin donor fused to an immunoglobulin gene acceptor) and the SV40 polyadenylation sequence and was transferred in sense orientation in the E1 region or in alternative orientations in the E3 region of the viral backbone. Some of these vectors generate RID complex-specific mRNAs of the expected molecular weight (approximately 1650 bases) in A549 cells. However, none show any RID-associated function in that it is impossible to detect any significant inhibition of Fas- or TNFa-mediated apoptosis, nor any down-modulation of the EGFR from the cell surface at any of the MOI tested (ranging from 10 to 500).

The second series of vectors was obtained by cloning the AflIII-XbaI DNA fragment of the Ad5 E3 region in the expression cassette described above. This segment covers from 35 base pairs (bp) upstream of the 10.4K initiation codon to 12 bp downstream of the 14.5K stop codon. These vectors are represented in FIG. 1, RID(E1+) referring to insertion in sense orientation in place of the deleted adenoviral E1 region, RID(E3+) referring to insertion in sense orientation in place of the deleted adenoviral E3 region and RID(E3−) referring to insertion in anti-sense orientation in place of the deleted adenoviral E3 region. A RID-specific mRNA of the expected 1100 nucleotide length is detected for every construct in infected A549 cells with the vector expressing the RID cassette from the E3 region in sense orientation (RID(E3+)) showing larger amounts of RID-specific message that the two other vectors (RID (E1+) and RID (E3−)) When tested in vitro for RID complex-associated functions, important variations are seen between the different constructs. All vectors can inhibit Fas-mediated apoptosis and down-modulate the EGFR, although with varying efficiencies; the RID(E3+) vector being the most efficient for both parameters (92% inhibition of Fas-induced apoptosis relative to positive control compared to 73% and 58% inhibition for the RID(E1+) and the RID(E3−), respectively); (81% down-modulation of EGFr relative to wild type levels of expression compared to the other vectors (44% and 52% for the RID(E1+) and the RID(E3−), respectively). Also, the RID(E3+) vector is capable of inhibiting TNFα-induced apoptosis.

B. In vivo Functionality of the RID-expressing Vector

Levels and duration of expression of the RID-complex mRNA were evaluated in mouse livers after intravenous injection or in the lung after intratracheal injection of $2 \times 10^9$ infectious units of each vector. Total RNA was extracted from target organs and probed by Northern blotting for RID-complex specific mRNAs. The pattern of mRNA seen in transduced livers or lungs correspond closely to what is seen in vitro for each of the vectors. For the same amount of total RNA obtained from organs taken from animals receiving the same amount of the various vectors, no obvious difference was seen in the intensity of the RID-specific signal. For all vectors and in both organs, RID-complex expression was detected for at least day 15 post-injection.

C. Protection from Fas-induced Acute Hepatitis by RID-expressing Vectors

Figure 2:
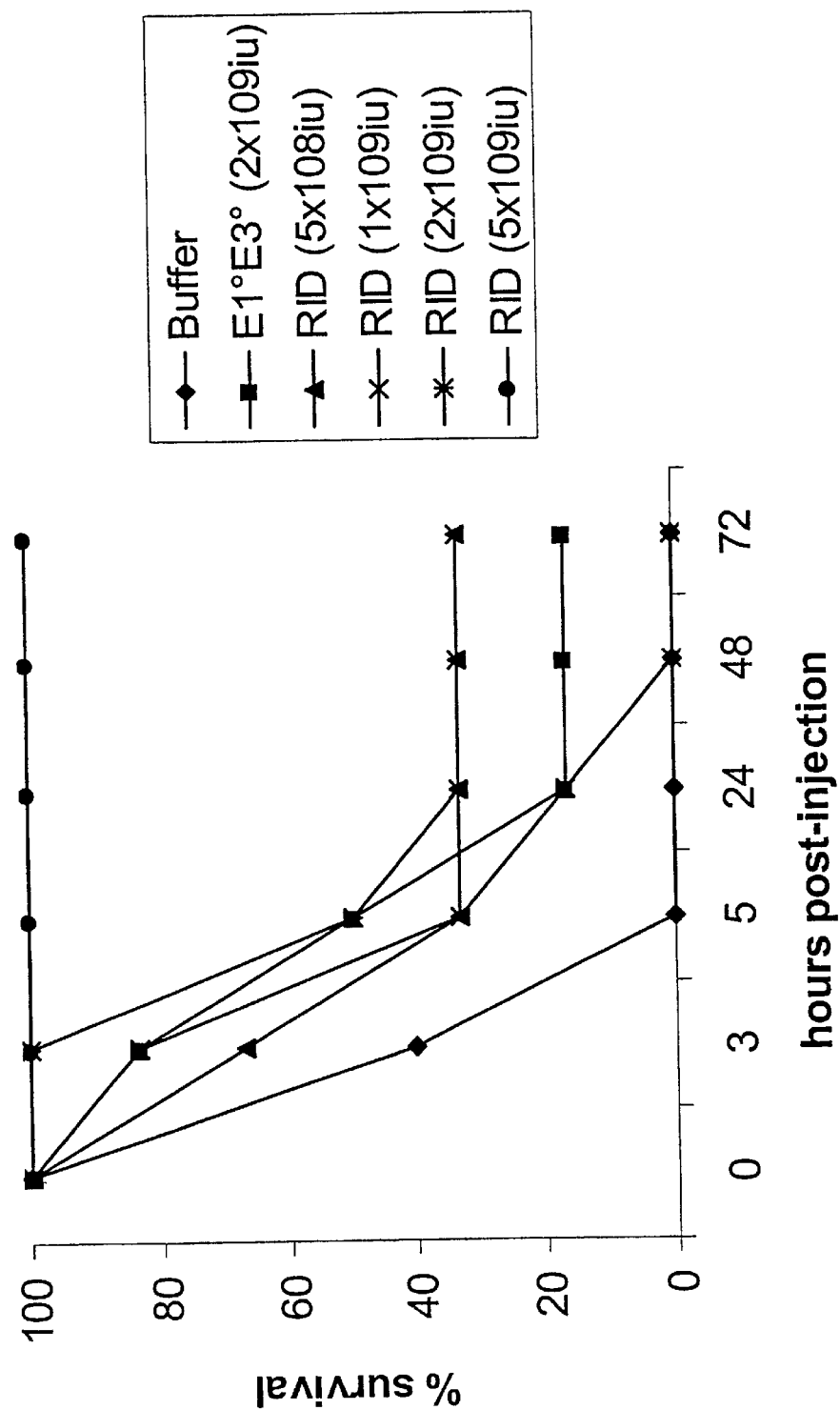
FIG. 2 illustrates the in vivo performance of the RID-expressing adenoviral vector in an acute hepatitis model. Increasing doses of RID (E3+) vector or negative controls (buffer or a E1 and E3 deleted vector) were injected intravenouly to mice. Five days later, lethal doses of anti-Fas antibodies were administered to the mice and mortality monitored.

Because the RID-complex is known to inhibit TNF- and Fas-induced apoptosis, we evaluated the in vivo performance of RID-constitutive vectors in two acute hepatitis models. Briefly, mice were challenged with lethal doses of LPS or of anti-Fas antibody five days after being injected intravenously either with control or RID-constitutive vectors. In a preliminary experiment, $2 \times 10^9$ IU of each of the in vitro functional, RID-expressing vectors were injected. Five days later, lethal doses of either LPS or of the anti-Fas antibody were administered and mortality monitored. While none of the RID expressing vectors had an anti-LPS effect, the CMV-RID(E3+) vector is capable of protecting animals injected with the anti-Fas antibody. A dose response experiment showed that a higher dose of this vector ($5 \times 10^9$ IU) can fully protect Fas-challenged animals (FIG. 2).

Pathological analysis of anti-Fas-treated livers sampled from buffer or control vector-injected animals show levels of coagulative necrosis and tissue degeneration that preclude further description of pathological markers. Alternatively, livers from animals protected from anti-Fas-induced death by transduction with RID-expressing vector show less extensive tissue damage and retained liver organization. The main pathological features seen in these organs are single cell necrosis and sinusoidal inflammatory aggregation. The in situ cell death assay reveals generalized and extensive apoptosis/necrosis in unprotected livers. Livers in protected (surviving) animals have few apoptotic cells with small numbers of cytoplasmically labelled cells. However, a large proportion of nuclei in protected organs are stained, indicating extensive tissue regeneration. In another set of experiment, animals were allowed to live beyond the 3 day post-challenge time point. All the animals that survive at day 3 after anti-Fas injection lived for at least 8 days beyond that point. This rules out the possibility that expression of the RID proteins simply retards LPS-mediated apoptosis of hepatocytes and argues in favor of bona fide protection.

Example 2

Functionality of the 14.7K-expressing Vectors

A. In vitro Functionality of the 14.7K Expressing Vectors

Figure 3:
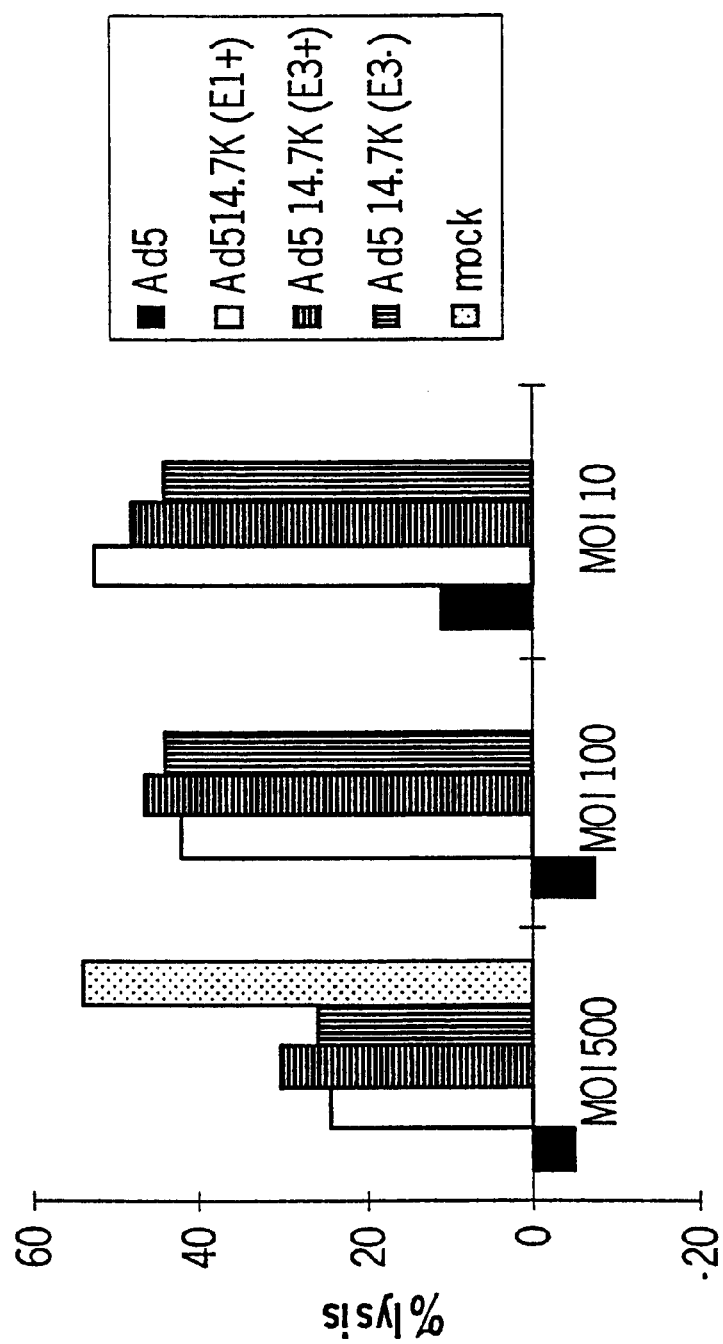
FIG. 3 illustrates the inhibition of TNFα-induced apoptosis in vitro. A549 cells were infected with the indicated vectors 24 hours prior to being exposed to cycloheximine and TNFα. 16 hours later, supernatant was collected and a colometric assay to measure lysis was performed (Cytotox96, Promega). Results are means of triplicate and are expressed in % of lysis=[(OD value of test)−(OD value of spontaneous release)×100]: [OD value of 100% lysis)−(OD value of spontaneous release)].
Figure 4:
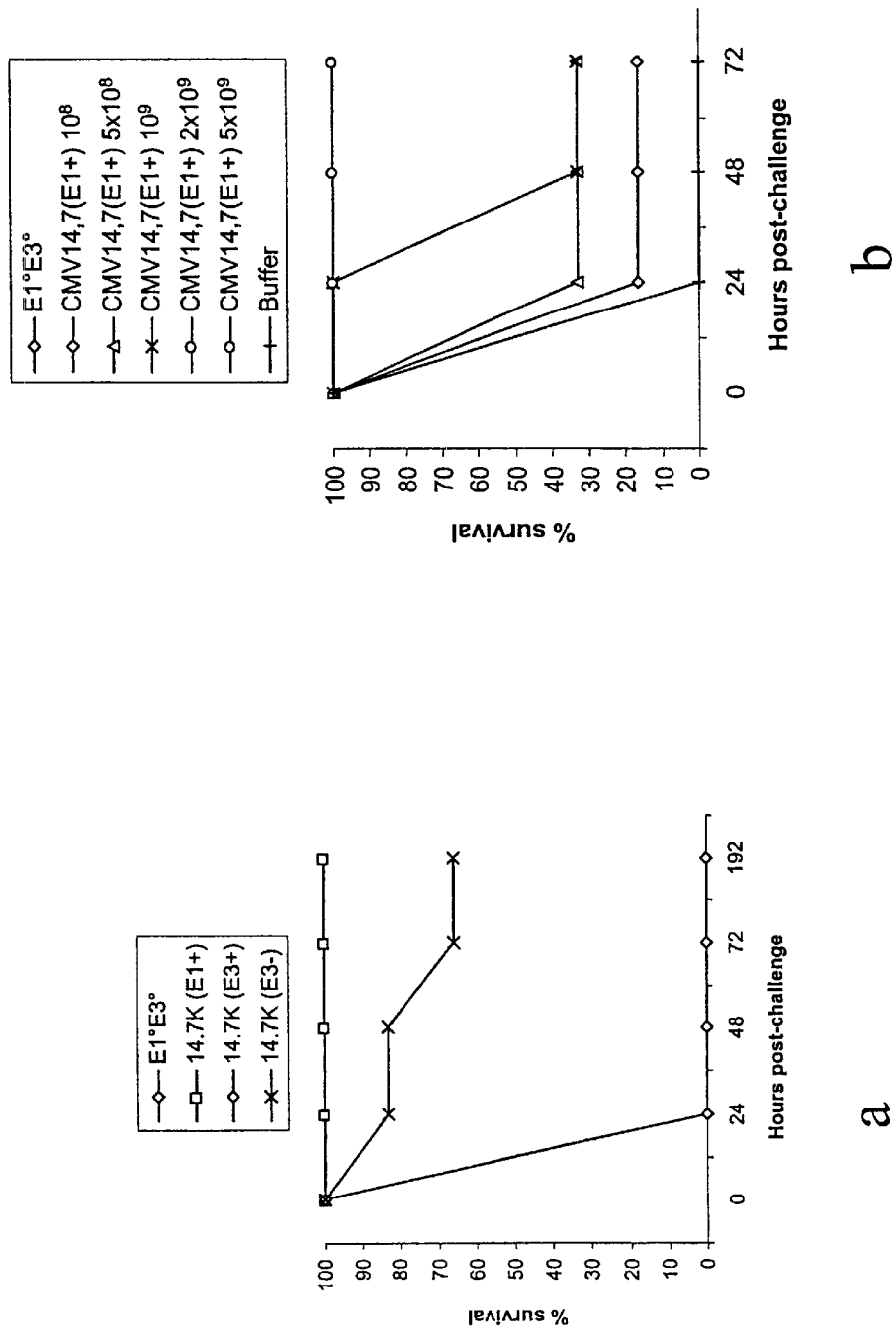
FIG. 4 illustrates the in vivo performance of the 14.7K-expressing adenoviral vectors in an acute hepatitis model. (a) Mice were challenged with a lethal dose of galactosamine and LPS five days after being injected intravenously with either a E1 and E3 deleted vector (negative control) or the different 14.7K expressing vectors and mortality monitored. (b) Increasing doses of 14.7K (E1+) vector or negative controls (buffer or a E1 and E3 deleted vector) were injected intravenouly to mice. Five days later, lethal doses of LPS were administered to the mice and mortality monitored.

As summarized in FIG. 1, three adenoviral constructs were generated. Because of the complex splicing pattern of E3-region encoded mRNA transcribed from the endogenous E3 promoter, we first looked for efficient expression from various cassettes placed in different orientations and regions relative to the vector backbone (14.7K (E1+), 14.7K(E3+) and 14.7K(E3−)). The only constructs that give 14.7K-specific mRNA of expected molecular weight (about 770 nucleotides) in A549 cells, are the vectors that make use of the CMV promoter, the pCI chimeric intron and the SV40 polyadenylation sequence. The same 3 vectors, at a MOI of 500, are capable of inhibiting TNFα-induced apoptosis to about 50% the values obtained in mock-infected cultures (FIG. 3). These vectors lose this function at a MOI lower than 200 in human cells. In a murine cell line (C3H), at a MOI of 100, the 14.7K-constitutive vectors are capable of inhibiting TNFa-induced apoptosis to about 80% the values induced in mock infected cells. Significant inhibition is also seen at a MOI as low as 50 (50% inhibition relative to mock infected cultures) (FIG. 4B).

B. In vivo Functionality of 14.7K-expressing Vectors

Levels and duration of expression of the 14.7K were evaluated in mouse livers. Total RNA was extracted from livers of intravenously injected animals and probed for 14.7K-specific mRNAs. The pattern of mRNA seen in livers transduced with 14.7K-constitutive vectors corresponds closely to what is seen in vitro. No obvious difference was seen in the 14.7K-specific signal in organs transduced with the same amount of the different vectors. In vivo expression is detectable up to 15 days post-injection by northern blotting.

C. Protection of LPS-induced Acute Hepatitis by the 14.7K-expressing Vectors

In order to determine if the 14.7K vectors could inhibit TNFα-mediated apoptosis in vivo, we used a mouse model of acute hepatitis. Briefly, mice were challenged with a lethal dose of LPS five days after being injected intravenously either with control or 14.7K-constitutive vectors. All buffer-injected or empty vector-injected animals (6 animals per group) died within 24 hours after injection of LPS (FIG. 4a). Of the 3 different constructs that inhibit TNF-induced apoptosis in human cell lines, the vector that expresses the 14.7K cDNA from the cassette placed in E1 in protected 100% of the animals. The vector with the expression cassette placed in anti-sense orientation in the E3 region of the vector shows partial protection while the one with the expression cassette in the sense orientation did not protect at all. These observations contrast with what is seen in vitro protection experiments in which all vectors perform similarly (see above). A dose response experiment showed that a dose of the vector 14.7K(E1+) of $2 \times 10^9$ IU can fully protect LPS-challenged animals (FIG. 4b).

Pathological analysis of LPS-treated livers sampled from buffer- or control vector injected moribund animals show levels of coagulative necrosis and tissue degeneration that preclude further description of pathological markers. Alternatively, livers from animals protected from LPS-induced death by transduction with a 14.7K-expressing vector show less extensive tissue damage and retained liver organization. The main pathological features seen in these organs are single cell necrosis and sinusoidal inflammatory aggregation. The in situ cell death assay reveals generalized and extensive apoptosis/necrosis in unprotected livers. Livers in protected (surviving) animals have few apoptotic cells with small numbers of cytoplasmically labeled cells. However, a large proportion of nuclei in protected organs are stained, indicating extensive tissue regeneration. In another set of experiment animals were allowed to live beyond the 3 day post-challenge time point. All the animals that survive at day 3 after LPS injection lived for at least 8 days beyond that point. This observation rules out the possibility that expression of the 14.7K merely retards apoptosis of hepatocytes.

What is claimed is:

1. A recombinant adenoviral vector in which at least a part of the E3 region is deleted or is rendered non-functional, wherein said adenoviral vector retains E3 sequences encoding:
   (i) a functional 14.7K protein, and optionally
   (ii) a functional 14.5K protein and a functional 10.4K protein, wherein said recombinant adenoviral vector comprises a gene of interest; wherein said retained E3 sequences and said gene of interest are operably linked to regulatory elements allowing their expression in a host cell; wherein said retained E3 sequences encoding a functional 14.7K protein are located in said adenoviral vector either (i) at a location where the E3 region normally resides and in anti-sense orientation relative to the direction of transcription of the native E3 region or (ii) wherein the E1 region normally resides and in sense orientation relative to the direction of transcription of the native E1 region; and wherein said retained E3 sequences encoding a functional 14.5K protein and a functional 10.4K protein are located in said adenoviral vector at a location where the E3 region normally resides and in sense orientation relative to the direction of transcription of the native E3 region.

2. The recombinant adenoviral vector of claim 1, wherein all of the E3 region is deleted or is rendered non-functional, with the exception of the E3sequence encoding functional 14.7K protein.

3. The recombinant adenoviral vector of claim 1, wherein all of the E3 region is deleted or is rendered non-functional, with the exception of the E3 sequences encoding functional 14.7K, 14.5K and 10.4K proteins.

4. The recombinant adenoviral vector of claim 3, wherein the functional 14.5K and 10.4K proteins associate in a host cell to form a receptor internalization and degradation complex (RID complex).

5. The recombinant adenoviral vector of claim 1, wherein the retained E3 sequences are placed under the control of the immediate early promoter of the cytomegalovirus (CMV promoter).

6. A method for preparing a viral particle, comprising:
   (i) introducing the adenoviral vector of claim 1, into a permissive cell, to obtain a transfected permissive cell;
   (ii) culturing said transfected permissive cell for an appropriate period of time and under suitable conditions to allow the production of said viral particle;
   (iii) recovering said viral particle from the cell culture; and
   (iv) optionally, purifying said recovered viral particle.

7. A viral particle comprising the adenoviral vector of claim 1.

8. An islolated host cell comprising the adenoviral vector of claim 1.

9. A composition comprising the adenoviral vector of claim 1 and a carrier therefor.

10. The recombinant adenoviral vector of claim 1, in which all or part of the E1 region is deleted or is rendered non-functional.

11. The recombinant adenoviral vector of claim 10, where at least one gene of the E2, E4, and L1–L5 regions is deleted or rendered non-functional.

12. The recombinant adenoviral vector of claim 1, in which all or part of the E1 region and all of the native E3 region are deleted or rendered non-functional, wherein the recombinant adenovial vector is a modified adenovirus genome of human adenovirus 5 (Ad5) and said retained E3sequences are isolated from the genome of the human adenovirus 2 (Ad2).

13. The recombinant adenoviral vector of claim 12, wherein at least one gene of the E2, E4, and L1–L5 regions is deleted or rendered non-functional.

* * * * *